United States Patent [19]

Weinshank et al.

[11] Patent Number: 5,360,735
[45] Date of Patent: Nov. 1, 1994

[54] DNA ENCODING A HUMAN 5-$HT_{1F}$ RECEPTOR, VECTORS, AND HOST CELLS

[75] Inventors: Richard L. Weinshank, New York, N.Y.; Theresa Branchek, Teaneck; Paul R. Hartig, Mahwah, both of N.J.

[73] Assignee: Synaptic Pharmaceutical Corporation, Paramus, N.J.

[21] Appl. No.: 817,920

[22] Filed: Jan. 8, 1992

[51] Int. Cl.$^5$ .............. C12N 5/00; C12N 15/00; C12N 1/20; C12N 1/16
[52] U.S. Cl. .............. 435/240.2; 435/172.1; 435/252.3; 435/254.11; 435/320.1; 536/23.5
[58] Field of Search ................ 536/27, 23.5; 435/240.2, 252.3, 172.1, 6, 320.1, 69.1

[56] References Cited

U.S. PATENT DOCUMENTS 5,155,218  10/1992  Weinshank et al. ............... 536/27

OTHER PUBLICATIONS

Schwab, E. F. et al. *Soc. Neurosci. Abstr.*, 15(1): 546, 1989, Abstract 222.9.

Weisberg et al., *Drug Development Research*, 26(3): 225-234, 1992.

Leonhardt, S. et al., *J. Neurochem.*, 53(2): 465-71, 1989.

*Primary Examiner*—Robert J. Hill, Jr.
*Assistant Examiner*—Marianne Porta Allen
*Attorney, Agent, or Firm*—John P. White

[57] ABSTRACT

This invention provides an isolated nucleic acid molecule encoding a human 5-$HT_{1F}$ receptor, an isolated protein which is a human 5-$HT_{1F}$ receptor, vectors comprising an isolated nucleic acid molecule encoding a human 5-$HT_{1F}$ receptors, mammalian cells comprising such vectors, antibodies directed to the human 5-$HT_{1F}$ receptor, nucleic acid probes useful for detecting nucleic acid encoding human 5-$HT_{1F}$ receptors, antisense oligonucleotides complementary to any sequences of a nucleic acid molecule which encodes a human 5-$HT_{1F}$ receptor, pharmaceutical compounds related to human 5-$HT_{1F}$ receptors, and nonhuman transgenic animals which express DNA a normal or a mutant human 5-$HT_{1F}$ receptor. This invention further provides methods for determining ligand binding, detecting expression, drug screening, and treatment involving the human 5-$HT_{1F}$ receptor.

13 Claims, 7 Drawing Sheets

FIGURE 1A

```
        -610                  -590                  -570
TTGCATGCCTGCAGGTCGACTCTAGAGGATCCCCGGGTACCGAGCTCGAATTCCTTTGTT
        -550                  -530                  -510
ATTTTGTCATGCTTCAAGCCTAGGAAAAGCCTAAGCAAAACTCTTGGTGGGCTCTTTGTT
        -490                  -470                  -450
ACATTCCAGCCTTTGAATAAGGGCACTGGCTCTATCAGCTTTGAATATATAACTCAACTA
        -430                  -410                  -390
GTCAGTCAGTAGTACTGAAACAGTTGTTACGGAGGCCTGCGTTATTGAGATCGGGCCTGC
        -370                  -350                  -330
CACACTTTTAAACTTTTTCTGACATGGACAAAGAGAAAAACCAATTCTATAATGGCAGAG
        -310                  -290                  -270
ATTTCACTGAGTAACAAGCTAGAGTATCATTAAAAATTGTTGTATTTAACCTATATTTTA
        -250                  -230                  -210
AGAAATGTTTTGGAAGTTACTGGCTTTTTTTACTGTTCTCATTAAATTTCTTAAATAAAA
        -190                  -170                  -150
AGGAAAACTAAAACCTTCAATCTGAACCTCATTTTTTTAATCTATAGAATATTCTGGGTA
        -130                  -110                   -90
AACATAACATACACTTTTTAAAAATTATTCTGAAAGGAAGAGAAAAGTTCTTGAAGCCTT
         -70                   -50                   -30
CTCTGAACTGTTTTTTCTCTTCCCTTGTTACAGGTATCCATTTTTCAGCTATATTAATCT
         -10                    10                    30
TTTAAAACAAAGAAAATGGATTTCTTAAATTCATCTGATCAAAACTTGACCTCAGAGGAA
              M  D  F  L  N  S  S  D  Q  N  L  T  S  E  E
```

FIGURE 1B

```
          50                        70                        90
CTGTTAAACAGAATGCCATCCAAAATTCTGGTGTCCCTCACTCTGTCTGGGCTGGCACTG
  L  L  N  R  M  P  S  K  I  L  V  S  L  T  L  S  G  L  A  L 110                       130                       150
ATGACAACAACTATCAACTCCCTTGTGATCGCTGCAATTATTGTGACCCGGAAGCTGCAC
  M  T  T  I  N  S  L  V  I  A  A  I  I  V  T  R  K  L  H 170                       190                       210
CATCCAGCCAATTATTTAATTTGTTCCCTTGCAGTCACAGATTTTCTTGTGGCTGTCCTG
  H  P  A  N  Y  L  I  C  S  L  A  V  T  D  F  L  V  A  V  L 230                       250                       270
GTGATGCCCTTCAGCATTGTGTATATTGTGAGAGAGAGCTGGATTATGGGGCAAGTGGTC
  V  M  P  F  S  I  V  Y  I  V  R  E  S  W  I  M  G  Q  V  V 290                       310                       330
TGTGACATTTGGCTGAGTGTTGACATTACCTGCTGCACGTGCTCCATCTTGCATCTCTCA
  C  D  I  W  L  S  V  D  I  T  C  C  T  C  S  I  L  H  L  S 350                       370                       390
GCTATAGCTTTGGATCGGTATCGAGCAATCACAGATGCTGTTGAGTATGCCAGGAAAAGG
  A  I  A  L  D  R  Y  R  A  I  T  D  A  V  E  Y  A  R  K  R 410                       430                       450
ACTCCAAAGCATGCTGGCATTATGATTACAATAGTTTGGATTATATCTGTTTTTATCTCT
  T  P  K  H  A  G  I  M  I  T  I  V  W  I  I  S  V  F  I  S 470                       490                       510
ATGCCTCCTCTATTCTGGAGGCACCAAGGAACTAGCAGAGATGATGAATGCATCATCAAG
  M  P  P  L  F  W  R  H  Q  G  T  S  R  D  D  E  C  I  I  K 530                       550                       570
CACGACCACATTGTTTCCACCATTTACTCAACATTTGGAGCTTTCTACATCCCACTGGCA
  H  D  H  I  V  S  T  I  Y  S  T  F  G  A  F  Y  I  P  L  A
```

FIGURE 1C

```
       590                  610                    630
TTGATTTTGATCCTTTACTACAAAATATATAGAGCAGCAAAGACATTATACCACAAGAGA
 L  I  L  I  L  Y  Y  K  I  Y  R  A  A  K  T  L  Y  H  K  R
       650                  670                    690
CAAGCAAGTAGGATTGCAAAGGAGGAGGTGAATGGCCAAGTCCTTTTGGAGAGTGGTGAG
 Q  A  S  R  I  A  K  E  E  V  N  G  Q  V  L  L  E  S  G  E
       710                  730                    750
AAAAGCACTAAATCAGTTTCCACATCCTATGTACTAGAAAAGTCTTTATCTGACCCATCA
 K  S  T  K  S  V  S  T  S  Y  V  L  E  K  S  L  S  D  P  S
       770                  790                    810
ACAGACTTTGATAAAATTCATAGCACAGTGAGAAGTCTCAGGTCTGAATTCAAGCATGAG
 T  D  F  D  K  I  H  S  T  V  R  S  L  R  S  E  F  K  H  E
       830                  850                    870
AAATCTTGGAGAAGGCAAAAGATCTCAGGTACAAGAGAACGGAAAGCAGCCACTACCCTG
 K  S  W  R  R  Q  K  I  S  G  T  R  E  R  K  A  A  T  T  L
       890                  910                    930
GGATTAATCTTGGGTGCATTTGTAATATGTTGGCTTCCTTTTTTTGTAAAAGAATTAGTT
 G  L  I  L  G  A  F  V  I  C  W  L  P  F  F  V  K  E  L  V
       950                  970                    990
GTTAATGTCTGTGACAAATGTAAAATTTCTGAAGAAATGTCCAATTTTTTGGCATGGCTT
 V  N  V  C  D  K  C  K  I  S  E  E  M  S  N  F  L  A  W  L
       1010                 1030                   1050
GGGTATCTCAATTCCCTTATAAATCCACTGATTTACACAATCTTTAATGAAGACTTCAAG
 G  Y  L  N  S  L  I  N  P  L  I  Y  T  I  F  N  E  D  F  K
       1070                 1090                   1110
AAAGCATTCCAAAAGCTTGTGCGATGTCGATGTTAGTTTTAAAAATGTTT
 K  A  F  Q  K  L  V  R  C  R  C
```

FIGURE 2A

```
              1                                                          50
5HT1C         M.......... .......... ...VNLGNAV RSLLMHLIGL LVWQFDISIS
5HT2          MDILCEENTS LSSTTNSLMQ LNDDTRLYSN DFNSGEANTS DAFNWTVDSE
5HT1Dα        M.......... .......... .......... ......SPLN QSAEGLPQEA
5HT1Dβ        M.......... .......... ........EE PGAQCAPPPP AGSETWVPQA
5HT1F         M.......... .......... .......... .......... .DVLSPGQGN
5HT1A         M.......... .......... .......... .......... ..........
TM Region 51                                                        100
5HT1C         PVAAIVTDTF NSSDGGRLFQ FPDGVQNWPA LSIVVIIIMT IGGNILVIMA
5HT2          NRTNLSCEGC LSPSCLSLLH LQE..KNWSA LLTAVIILT  IAGNILVIMA
5HT1Dα        ...SNRSLNA TETSEAWDPR TLQALKISLA VVLSVITLAT VLSNAFVLTT
5HT1Dβ        NLSSAPSQNC SAKDYIYQDS ISLPWKVLLV MLLALITLAT TLSNAFVIAT
5HT1F         ....DFLNSS DQNLTSEELL NRMPSKILVS LTLSGLALMT TTINSLVIAA
5HT1A         NTTSPPAPFE TGGNTTGISD VTVSYQVITS LLLGTLIFCA VLGNACVVAA
TM Region     .......... .......... .....***** *********. I..*******
```

FIGURE 2B

```
          101                                                           150
5HT₁C     VSMEKKLHNA  TNYFLMSLAI  ADMLVGLLVM  PLSLLAILYD  YVWPLPRYLC
5HT₂      VSLEKKLQNA  TNYFLMSLAI  ADMLLGFLVM  PVSMLTILYG  YRWPLPSKLC
5HT₁Dα    ILLTRKLHTP  ANYLIGSLAT  TDLLVSILVM  PISMAYTITH  .TWNFGQILC
5HT₁Dβ    VYRTRKLHTP  ANYLIASLAV  TDLLVSILVM  PISTMYTVTG  .RWTLGQVVC
5HT₁F     IIVTRKLHHP  ANYLICSLAV  TDFLVAVLVM  PFSIVYIVRE  .SWIMGQVVC
5HT₁A     IALERSLQNV  ANYLIGSLAV  TDLMVSVLVL  PMAALYQVLN  .KWTLGQVTC
TM Region *.........  ..*.*******  ***...II..*  .........  .........

151                                                           200
5HT₁C     PVWISLDVLF  STASIMHLCA  ISLDRYVAIR  NPIEHSRFNS  RTKAIMKIAI
5HT₂      AVWIYLDVLF  STASIMHLCA  ISLDRYVAIQ  NPIHHSRFNS  RTKAFLKIIA
5HT₁Dα    DIWLSSDITC  CTASILHLCV  IALDRYWAIT  DALEYSKRRT  AGHAATMIAI
5HT₁Dβ    DFWLSSDITC  CTASILHLCV  IALDRYWAIT  DAVEYSAKRT  PKRAAVMIAL
5HT₁F     DIWLSVDITC  CTCSILHLSA  IALDRYRAIT  DAVEYARKRT  PKHAGIMITI
5HT₁A     DLFIALDVLC  CTSSILHLCA  IALDRYWAIT  DPIDYVNKRT  PRRAAALISL
TM Region .********.  .***......  .***......  .........  ******....

201                                                           250
5HT₁C     VWAISIGVSV  PIPVIGLRDE  SKVFVNNTTC  VLNDP.NFVL  IGSFVAFFIP
5HT₂      VWTISVGISM  PIPVFGLQDD  SKVF.KEGSC  LLADD.NFVL  IGSFVSFFIP
5HT₁Dα    VWAISICISI  P.PLF.WRQA  KAQEEMSDCL  VNTSQISYTI  YSTCGAFYIP
5HT₁Dβ    VWVFSISISL  P.PFF.WRQA  KAEEEVSECV  VNTDHILYTV  YSTVGAFYFP
5HT₁F     VWIISVFISM  P.PLF.WRHQ  GTSRD.DECI  IKHDHIVSTI  YSTFGAFYIP
5HT₁A     TWLIGFLISI  P.PMLGWRTP  EDRSDPDACT  ISKDH.GYTI  YSTFGAFYIP
TM Region ***.......  *******...  .........  .........  *****..V.
```

FIGURE 2C

```
               251
5HT1C          LTIMVITYFL  TI.....YVL  RRQTLMLLRG  .HTEEELANM  SLNFLNCCCK
5HT2           LTIMVITYFL  TI.....KSL  QKEATLCVSD  LGTRAKLA..  SFSFLPQSSL
5HT1Dα         SVLLIILYGR  IYRAARNRIL  .NPPSLYGKR  FTTAHLITGS  .G..SSLCSL
5HT1Dβ         TLLLIALYGR  IYVEARSRIL  KQTPNRTGKR  LTRAQLITDS  PGSTSSVTSI
5HT1F          LALILILYYK  IYRAAKTLYH  KRQASRIAKE  EVNGQVLLES  GE..KSTKSV
5HT1A          LLLMLVLYGR  IFRAARFRIR  KTVKKVEKTG  ADTRHGASPA  PQPKKSVNGE
TM Region      .********.  ..........  ..........  ..........  ..........

301                                                    350
5HT1C          KNGGEEENAP  NPNPDQ..KP  RRKKKEKRPR  GTMQ......  ..........
5HT2           SSEKLFQRSI  HREPGS..YT  GRR.......  .TMQ......  ..........
5HT1Dα         NSS..LHEGH  SHSAGSPLFF  N.HVKIKLAD  SALE......  ..........
5HT1Dβ         NSR..VPDVP  SES.GSPVYV  N.QVKVRVSD  ALLE......  ..........
5HT1F          STS..YVLEK  SLSDPSTDFD  KIHSTVRSLR  SEFKHEKSWR  ..........
5HT1A          SGSRNWRLGV  ESKAGGALCA  NGAVRQGDDG  AALEVIEVHR  VGNSKEHLPL
TM Region      ..........  ..........  ..........  ..........  ..........

351                                                    400
5HT1C          ..........  ..........  ........AI  NNEKKASKVL  GIVFFVFLIM
5HT2           ..........  ..........  ........SI  SNEQKACKVL  GIVFFLFVVM
5HT1Dα         ..........  ..........  ....RKRISA  ARERKATKIL  GIILGAFIIC
5HT1Dβ         ..........  ..........  ....KKKLMA  ARERKATKTL  GIILGAFIVC
5HT1F          ..........  ..........  ....RQKISG  TRERKAATTL  GLILGAFVIC
5HT1A          PSEAGPTPCA  PASFERKNER  NAEAKRKMAL  ARERKTVKTL  GIIMGTFILC
TM Region      ..........  ..........  ..........  .*........  .********.
```

FIGURE 2D

```
            401                                                          450
5HT1C       WCPFFITNIL  SVLCGKACNQ  KLMEKLLNVF  VWIGYVCSGI  NPLVYTLFNK
5HT2        WCPFFITNIM  AVICKESCNE  DVIGALLNVF  VWIGYLSSAV  NPLVYTLFNK
5HT1Dα      WLPFFVVSLV  LPICRDSCW.  .IHPGLFDFF  TWLGYLNSLI  NPIIYTVFNE
5HT1Dβ      WLPFFIISLV  MPICKDACW.  .FHLAIFDFF  TWLGYLNSLI  NPIIYTMSNE
5HT1F       WLPFFVKELV  VNVC.DKCK.  .ISEEMSNFL  AWLGYLNSLI  NPLIYTIFNE
5HT1A       WLPFFIVALV  LPFCESSCH.  .MPTLLGAII  NWLGYSNSLL  NPVIYAYFNK
TM Region   VI..******  **........  ...*******  ***..VII..  *********..

451                                                          500
5HT1C       IYRRAFSKYL  RCDYKPDKKP  .PVRQIPRVA  ATALSGRELN  VNIYRHTNER
5HT2        TYRSAFSRYI  QCQYKENKKP  LQLILVNTIP  ALAYKSSQLQ  MGQKKNSKQD
5HT1Dα      EFRQAFQKIV  PFRKAS....  ..........  ..........  ..........
5HT1Dβ      DFKQAFHKLI  RFICCTS...  ..........  ..........  ..........
5HT1F       DFKKAFQKLV  RCRC......  ..........  ..........  ..........
5HT1A       DFQNAFKKII  KCLFCRQ...  ..........  ..........  ..........
TM Region   ..........  ..........  ..........  ..........  ..........

501                  537
5HT1C       VARKANDPEP  GIEMQVENLE  LPVNPSNVVS  ERISSV.
5HT2        AKTTDNDCSM  VALGKQHSEE  ASKDNSDGVN  EKVSCV.
5HT1Dα      ..........  ..........  ..........  .......
5HT1Dβ      ..........  ..........  ..........  .......
5HT1F       ..........  ..........  ..........  .......
5HT1A       ..........  ..........  ..........  .......
TM Region   ..........  ..........  ..........  .......
```

DNA ENCODING A HUMAN 5-HT$_{1F}$ RECEPTOR, VECTORS, AND HOST CELLS

BACKGROUND OF THE INVENTION

Since the purification of a pressor substance in blood serum termed serotonin (Rapport et al., 1947) and later identified as 5-hydroxytryptamine (5-HT)(Rapport, 1949), there has been a plethora of reports demonstrating that this indoleamine not only plays a role in the functioning of peripheral tissues but, indeed, performs a key role in the brain as a neurotransmitter. Certainly, the anatomical localization of serotonin and serotonergic neurons in both the peripheral and central nervous systems supports its role in such diverse physiologic and behavioral functions as pain perception, sleep, aggression, sexual activity, hormone secretion, thermoregulation, motor activity, cardiovascular function, food intake and renal regulation (For review see Green, 1985; Osborne and Hamon, 1988; Sanders-Bush, 1988; Peroutka, 1991). Taken together, it appears that serotonin plays an important role in homeostasis and in modulating responsiveness to environmental stimuli. Accordingly, studies demonstrating that abnormalities in the serotonergic system may be associated with disease states has created a drug development effort towards agents which may selectively modulate the function of serotonin (Glennon, 1990).

In relation to the characterization of physiologic or biochemical responses resulting from the release of serotonin are simultaneous investigations examining the receptor sites responsible for the actions elicited by the indoleamine transmitter. Following early in vitro pharmacological assays describing the existence of two different serotonin receptors, designated as D and M, in the guinea pig ileum (Gaddum and Picarelli, 1957), the advent of receptor binding technique in the 1970's has brought to light during the last decade the diversity of 5-HT receptors existing in both the brain and peripheral tissues. Thus, although the concept of D and M receptors has not been invalidated, serotonin receptors not fitting either category have been identified using radioligand methods. To date using this technique, there appears to be four classes of serotonin receptors found in the brain: 5-HT$_1$, 5-HT$_2$, 5-HT$_3$ and, putatively, 5-HT$_4$(Peroutka, 1991). Furthermore, 5-HT$_1$ sites have been subclassified as: 5-HT$_{1A}$, 5-HT$_{1B}$, 5-HT$_{1C}$, 5-HT$_{1D}$ (Hamon et al., 1990) and 5-HT$_{1E}$ (Leonhardt et al., 1989). Although a detailed characterization of the 5-HT$_{1F}$ binding site is lacking, extensive pharmacologic, biochemical and functional properties have clearly shown that the other four subtypes of 5-HT$_1$ sites are receptors according to classical criteria.

During the last few years, the field of molecular biology has provided an important facet to receptor research by cloning these proteins and allowing more precise characterizations in isolated systems (Hartig et al,1990). This has been accomplished for the 5-HT$_{1A}$ (Fargin et al., 1988), 5-HT$_{1C}$ (Julius et al., 1988), 5-HT$_{1D}$ (Branchek et al., 1990) and 5-HT$_2$ receptors (Pritchett et al., 1988). Thus, there is no doubt that these binding sites represent "true" functional receptors. Indeed, the pharmacological characterization of serotonin receptors involved in various physiological or biochemical functions is a key component of drug development for the serotonergic system. As one can deduce from the diversity of serotonin binding sites, many targets are available for advancement in selective drug design. The coupling of molecular biological methods to pharmacological characterization particularly for cloned human receptors will open new avenues for pharmaceutical development which has not been previously explored. This study is a pharmacological characterization of a serotonergic receptor clone with a binding profile different from that of any serotonergic receptor to date. In keeping with the nomenclature presently accepted for serotonin receptors, this novel site will be termed a 5-HT$_{1F}$ receptor based upon the fact that it possesses high affinity for the endogenous neurotransmitter, 5-HT.

SUMMARY OF THE INVENTION

This invention provides an isolated nucleic acid molecule encoding a human 5-HT$_{1F}$ receptor (Seq. I.D. No. 1).

This invention also provides an isolated protein which is a human 5-HT$_{1F}$ receptor (Seq. I.D. Nos. 2, 7).

This invention provides a vector comprising an isolated nucleic acid molecule encoding a human 5-HT$_{1F}$ receptor.

This invention also provides vectors such as plasmids comprising a DNA molecule encoding a human 5-HT$_{1F}$ receptor, adapted for expression in a bacterial cell, a yeast cell, or a mammalian cell which additionally comprise the regulatory elements necessary for expression of the DNA in the bacterial, yeast, or mammalian cells so located relative to the DNA encoding the 5-HT$_{1F}$ receptor as to permit expression thereof.

This invention provides a mammalian cell comprising a DNA molecule encoding a human 5-HT$_{1F}$ receptor.

This invention provides a method for determining whether a ligand not known to be capable of binding to a human 5-HT$_{1F}$ receptor can bind to a human 5-HT$_{1F}$ receptor which comprises contacting a mammalian cell comprising an isolated DNA molecule encoding a human 5-HT$_{1F}$ receptor with the ligand under conditions permitting binding of ligands known to bind to a 5-HT$_{1F}$ receptor, detecting the presence of any of the ligand bound to a human 5-HT$_{1F}$ receptor, and thereby determining whether the ligand binds to a human 5-HT$_{1F}$ receptor.

This invention also provides a method for determining whether a ligand not known to be capable of binding to the human 5-HT$_{1F}$ receptor can functionally activate its activity or prevent the action of a ligand which does so. This comprises contacting a mammalian cell comprising an isolated DNA molecule which encodes a human 5-HT$_{1F}$ receptor with the ligand under conditions permitting the activation or blockade of a functional response, detected by means of a bioassay from the mammalian cell such as a second messenger response, and thereby determining whether the ligand activates or prevents the activation of the human 5-HT$_{1F}$ receptor functional output.

This invention further provides a method of screening drugs to identify drugs which specifically interact with, and bind to, the human 5-HT$_{1F}$ receptor on the surface of a cell which comprises contacting a mammalian cell comprising an isolated DNA molecule encoding a human 5-HT$_{1F}$ receptor with a plurality of drugs, determining those drugs which bind to the mammalian cell, and thereby identifying drugs which specifically interact with, and bind to, a human 5-HT$_{1F}$ receptor.

This invention also provides a method of screening drugs to identify drugs which interact with, and activate or block the activation of, the human 5-HT$_{1F}$ receptor on the surface of a cell which comprises contacting the mammalian cell comprising an isolated DNA molecule encoding and expressing a human 5-HT$_{1F}$ receptor with a plurality of drugs, determining those drugs which activate or block the activation of the receptor in the mammalian cell using a bioassay such as a second messenger assays, and thereby identifying drugs which specifically interact with, and activate or block the activation of, a human 5-HT$_{1F}$ receptor.

This invention provides a nucleic acid probe comprising a nucleic acid molecule of at least 15 nucleotides capable of specifically hybridizing with a sequence included within the sequence of a nucleic acid molecule encoding a human 5-HT$_{1F}$ receptor.

This invention also provides a method of detecting expression of the 5-HT$_{1F}$ receptor on the surface of a cell by detecting the presence of mRNA coding for a 5-HT$_{1F}$ receptor which comprises obtaining total mRNA from the cell and contacting the mRNA so obtained with a nucleic acid probe comprising a nucleic acid molecule of at least 15 nucleotides capable of specifically hybridizing with a sequence included within the sequence of a nucleic acid molecule encoding a human 5-HT$_{1F}$ receptor under hybridizing conditions, detecting the presence of mRNA hybridized to the probe, and thereby detecting the expression of the 5-HT$_{1F}$ receptor by the cell.

This invention provides an antisense oligonucleotide having a sequence capable of binding specifically with any sequences of an mRNA molecule which encodes a human 5-HT$_{1F}$ receptor so as to prevent translation of the mRNA molecule.

This invention provides an antibody directed to a human 5-HT$_{1F}$ receptor.

This invention provides a transgenic nonhuman mammal expressing DNA encoding a human 5-HT$_{1F}$ receptor. This invention also provides a transgenic nonhuman mammal expressing DNA encoding a human 5-HT$_{1F}$ receptor so mutated as to be incapable of normal receptor activity, and not expressing native 5-HT$_{1F}$ receptor. This invention further provides a transgenic nonhuman mammal whose genome comprises antisense DNA complementary to DNA encoding a human 5-HT$_{1F}$ receptor so placed as to be transcribed into antisense mRNA which is complementary to mRNA encoding a 5-HT$_{1F}$ receptor and which hybridizes to mRNA encoding a 5-HT$_{1F}$ receptor thereby reducing its translation.

This invention provides a method of determining the physiological effects of expressing varying levels of human 5-HT$_{1F}$ receptors which comprises producing a transgenic nonhuman animal whose levels of human 5-HT$_{1F}$ receptor expression are varied by use of an inducible promoter which regulates human 5-HT$_{1F}$ receptor expression.

This invention also provides a method of determining the physiological effects of expressing varying levels of human 5-HT$_{1F}$ receptors which comprises producing a panel of transgenic nonhuman animals each expressing a different amount of human 5-HT$_{1F}$ receptor.

This invention provides a method for diagnosing a predisposition to a disorder associated with the expression of a specific human 5-HT$_{1F}$ receptor allele which comprises: a. obtaining DNA of subjects suffering from the disorder; b. performing a restriction digest of the DNA with a panel of restriction enzymes; c. electrophoretically separating the resulting DNA fragments on a sizing gel; d. contacting the resulting gel with a nucleic acid probe capable of specifically hybridizing to DNA encoding a human 5-HT$_{1F}$ receptor and labelled with a detectable marker; e. detecting labelled bands which have hybridized to the DNA encoding a human 5-HT$_{1F}$ receptor labelled with a detectable marker to create a unique band pattern specific to the DNA of subjects suffering from the disorder; f. preparing DNA obtained for diagnosis by steps a-e; and g. comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method of preparing the isolated 5-HT$_{1F}$ receptor which comprises inducing cells to express 5-HT$_{1F}$ receptor, recovering the receptor from the resulting cells and purifying the receptor so recovered.

This invention also provides a method of preparing the isolated 5-HT$_{1F}$ receptor which comprises inserting nucleic acid encoding 5-HT$_{1F}$ receptor in a suitable vector, inserting the resulting vector in a suitable host cell, recovering the receptor produced by the resulting cell, and purifying the receptor so recovered.

This invention provides an antisense oligonucleotide having a sequence capable of binding specifically with any sequences of an mRNA molecule which encodes a receptor so as to prevent translation of the mRNA molecule.

This invention also provides a transgenic nonhuman mammal expressing DNA encoding a receptor.

This invention further provides a transgenic nonhuman mammal expressing DNA encoding a receptor so mutated as to be incapable of normal receptor activity, and not expressing native receptor.

This invention also provides a method of determining the physiological effects of expressing varying levels of a receptor which comprises producing a transgenic nonhuman animal whose levels of receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides a transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding the receptor with the ligand under conditions permitting binding of ligands known to bind to a receptor, detecting the presence of any of the ligand bound to the receptor, and thereby determining whether the ligand binds to the receptor.

BRIEF DESCRIPTION OF THE FIGURES

FIGS. 1A–1C. These three consecutive figures disclose the nucleotide and deduced amino acid sequence of gene 5-HT$_{1F}$ (Seq. I.D. Nos. 1, 2, and 7).

Numbers above the nucleotide sequence indicate nucleotide position. DNA sequence was determined by the chain termination method of Sanger, et al., on denatured double-stranded plasmid templates using the enzyme Sequenase. Deduced amino acid sequence (single letter code) of a long open reading frame is shown.

FIGS. 2A–2D. These four consecutive figures disclose a comparison of the human 5-HT$_{1F}$ receptor primary structures with other serotonin receptors (Seq. I.D. Nos.: 5-HT$_{1F}$- 3; 5-HT$_{1C}$- 4; 5-HT$_{1D\alpha}$- 5; 5-HT$_{1D\beta}$- 6; 5-HT$_{1F}$- 7; 5-HT$_2$ - 8).

Amino acid sequences (single letter code) are aligned to optimize homology. The putative transmembrane spanning domains are indicated by stars and identified by Roman numerals (TM I–VII).

DETAILED DESCRIPTION OF THE INVENTION

As used herein, the 5-HT receptor family is defined as the group of mammalian proteins that function as receptors for serotonin. A 5-HT receptor subfamily is defined as a subset of proteins belonging to the 5-HT receptor family which are encoded by genes which exhibit homology of greater than 72% or higher with each other in their deduced amino acid sequences within presumed transmembrane regions (linearly contiguous stretches of hydrophobic amino acids, bordered by charged or polar amino acids, that are long enough to form secondary protein structures that span a lipid bilayer). Four human 5-HT receptor subfamilies can be distinguished based on the information presently available: 5-HT$_1$, 5-HT$_2$, 5-HT$_3$, and 5-HT$_4$ (Peroutka, 1991). The 5-HT$_2$ receptor subfamily contains the human 5-HT$_2$ receptor. Although no other human members of this family have been described, the rat 5-HT$_2$ receptor (Pritchett, et al. 1988; Julius, et al. Proc. Natl. Acad. Sci. USA 87:928–932, 1990) and the rat 5HT$_{1C}$ receptor (Julius, et al. 1988) constitute a rat 5-HT receptor subfamily. The 5-HT$_1$ subfamily has been subdivided further as: 5-HT$_{1A}$, 5-HT$_{1B}$, 5-HT$_{1C}$, 5-HT$_{1D}$ (Hamon et al., 1990) and 5-HT$_{1E}$ (Leonhardt et al., 1989). The 5-HT$_{1A}$ subfamily contains the human 5-HT$_{1A}$ receptor, also known as G-21 (Fargin, et al. 1988) The 5-HT$_{1D}$ receptor subfamily contains two members, the 5-HT$_{1D-1}$ receptor (also termed 5-HT$_{1D\alpha}$) and the 5-HT$_{1D-2}$ receptor (also termed 5-HT$_{1D\beta}$). The 5-HT$_{1F}$ subfamily contains the human 5-HT$_{1F}$ receptor (also termed clone h116a). Although this definition differs from the pharmacological definition used earlier, there is significant overlap between the present definition and the pharmacological definition. Members of the 5-HT$_{1F}$ receptor subfamily so described include the 5-HT$_{1F}$ receptor and any other receptors which have a greater than 72% homology to the DNA and amino acid sequence shown in FIGS. 1A–1C (Seq. I.D. Nos. 1, 2, and 7 ) according to the definition of "subfamily". This invention relates to the discovery of the first member of the human 5-HT$_{1F}$ receptor subfamily.

This invention provides an isolated nucleic acid molecule encoding a human 5-HT$_{1F}$ receptor (Seq. I.D. No. 1). As used herein, the term "isolated nucleic acid molecule" means a nucleic acid molecule that is, a molecule in a form which does not occur in nature. Such a receptor is by definition a member of the 5-HT$_{1F}$ receptor subfamily. Therefore, any receptor which meets the defining criteria given above is a human 5-HT$_{1F}$ receptor. One means of isolating a human 5-HT$_{1F}$ receptor is to probe a human genomic library with a natural or artificially designed DNA probe, using methods well known in the art. DNA probes derived from the human receptor gene 5-HT$_{1F}$ are particularly useful probes for this purpose. DNA and cDNA molecules which encode human 5-HT$_{1F}$ receptors may be used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clones, and other stability, processing, transcription, translation, and tissue specificity-determining regions from the 3' and 5' untranslated regions of the isolated genes are thereby obtained. Examples of a nucleic acid molecule are an RNA, cDNA, or isolated genomic DNA molecule encoding a human 5-HT$_{1F}$ receptor. Such molecules may have coding sequences substantially the same as the coding sequence shown in FIGS. 1A–1C. The DNA molecule of FIGS. 1A–1C encodes the sequence of the human 5-HT$_{1F}$ receptor gene (Seq. I.D. No. 1).

This invention further provides a cDNA molecule of encoding a human 5-HT$_{1F}$ receptor having a coding sequence substantially the same as the coding sequence shown in FIGS. 1A–1C (Seq. I.D. No. 1). This molecule is obtained by the means described above.

This invention also provides an isolated protein which is a human 5-HT$_{1F}$ receptor. As used herein, the term "isolated protein means a protein molecule free of other cellular components". An example of such protein is an isolated protein having substantially the same amino acid sequence as the amino acid sequence shown in FIGS. 1A–1C (Seq. I.D. Nos. 2, 7) which is a human 5-HT$_{1F}$ receptor. One means for obtaining isolated 5-HT$_{1F}$ receptor is to express DNA encoding the receptor in a suitable host, such as a bacterial, yeast, or mammalian cell, using methods well known in the art, and recovering the receptor protein after it has been expressed in such a host, again using methods well known in the art. The receptor may also be isolated from cells which express it, in particular from cells which have been transfected with the expression vectors described below in more detail.

This invention provides a vector comprising an isolated nucleic acid molecule such as DNA, RNA, or cDNA encoding a human 5-HT$_{1F}$ receptor. Examples of vectors are viruses such as bacteriophages (such as phage lambda), cosmids, plasmids (such as pUC1S, available from Pharmacia, Piscataway, NJ), and other recombination vectors. Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available. A specific example of such plasmids is a plasmid comprising cDNA having a coding sequence substantially the same as the coding sequence shown in FIGS. 1A–1C and designated clone h116a.

This invention also provides vectors comprising a DNA molecule encoding a human 5-HT$_{1F}$ receptor, adapted for expression in a bacterial cell, a yeast cell, or a mammalian cell which additionally comprise the regulatory elements necessary for expression of the DNA in the bacterial, yeast, or mammalian cells so located relative to the DNA encoding a human 5-HT$_{1F}$ receptor as to permit expression thereof. DNA having coding sequences substantially the same as the coding sequence shown in FIGS. 1A–1C may usefully be inserted into the vectors to express human 5-HT$_{1F}$ receptors. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the receptor. Certain uses for such cells are described in more detail below.

This invention further provides a plasmid adapted for expression in a bacterial, yeast, or, in particular, a mammalian cell which comprises a DNA molecule encoding a human 5-HT$_{1F}$ receptor and the regulatory elements necessary for expression of the DNA in the bacterial, yeast, or mammalian cell so located relative to the DNA encoding a human 5-HT$_{1F}$ receptor as to permit expression thereof. Some plasmids adapted for expression in a mammalian cell are pSVL (available from Pharmacia, Piscataway, NJ), pcEXV-3 (Miller J. and Getmain R.N., J. Exp. Med. 164:1478 (1986)) and pMO5 (Branchek, T. et al, Mol. Pharm. 38:604–609 (1990)). A specific example of such plasmid is a plasmid adapted for expression in a mammalian cell comprising cDNA having coding sequences substantially the same as the coding sequence shown in FIGS. 1A–1C and the regulatory elements necessary for expression of the DNA in the mammalian cell which is designated pMO5-h116a and deposited under ATCC Accession No. 75175. Those skilled in the art will readily appreciate that numerous plasmids adapted for expression in a mammalian cell which comprise DNA of encoding human 5-HT$_{1F}$ receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposit discussed supra, and the other deposits discussed herein, were made pursuant to, and in satisfaction of, the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a human 5-HT$_{1F}$ receptor, such as a mammalian cell comprising a plasmid adapted for expression in a mammalian cell, which comprises a DNA molecule encoding a human 5-HT$_{1F}$ receptor, the protein encoded thereby is expressed on the cell surface, and the regulatory elements necessary for expression of the DNA in the mammalian cell so located relative to the DNA encoding a human 5-HT$_{1F}$ receptor as to permit expression thereof. Numerous mammalian cells may be used as hosts, including, for example, the mouse fibroblast cell NIH3T3, CHO cells, HeLa cells, Ltk$^-$ cells, Y1 cells, etc. A particular example of an Ltk$^-$ cell is a cell designated L-5-HT$_{1F}$ and deposited under ATCC Accession No. CRL 10957 and comprises the plasmid designated pMO5-h116a. Another example is the murine fibroblast cell line designated N-5-HT$_{1F}$ and deposited under ATCC Accession No. CRL 10956. Expression plasmids such as that described supra may be used to transfect mammalian cells by methods well known in the art such as calcium phosphate precipitation, or DNA encoding these 5-HT$_{1F}$ receptors may be otherwise introduced into mammalian cells, e.g., by microinjection, to obtain mammalian cells which comprise DNA, e.g., cDNA or a plasmid, encoding either human 5-HT$_{1F}$ receptor.

This invention provides a method for determining whether a ligand not known to be capable of binding to a human 5-HT$_{1F}$ receptor can bind to a human 5-HT$_{1F}$ receptor which comprises contacting a mammalian cell comprising a DNA molecule encoding a human 5-HT$_{1F}$ receptor, the protein encoded thereby is expressed on the cell surface, with the ligand under conditions permitting binding of ligands known to bind to the 5-HT$_{1F}$ receptor, detecting the presence of any of the ligand bound to the 5-HT$_{1F}$ receptor, and thereby determining whether the ligand binds to the 5-HT$_{1F}$ receptor. This invention also provides a method for determining whether a ligand not known to be capable of binding to the human 5-HT$_{1F}$ receptor can functionally activate its activity or prevent the action of a ligand which does so. This comprises contacting a mammalian cell comprising an isolated DNA molecule which encodes a human 5-HT$_{1F}$ receptor with the ligand under conditions permitting the activation or blockade of a functional response, detected by means of a bioassay from the mammalian cell such as a second messenger response, and thereby determining lo whether the ligand activates or prevents the activation of the human 5-HT$_{1F}$ receptor functional output. The DNA in the cell may have a coding sequence substantially the same as the coding sequence shown in FIGS. 1A–1C preferably, the mammalian cell is nonneuronal in origin. An example of a nonneuronal mammalian cell is an Ltk$^-$ cell, in particular the Ltk$^-$ cell designated L-5-HT$_{1F}$. Another example of a non-neuronal mammalian cell to be used for functional assays is a murine fibroblast cell line, specifically the NIH3T3 cell designated N-5-HT$_{1F}$. The preferred method for determining whether a ligand is capable of binding to the human 5-HT$_{1F}$ receptor comprises contacting a transfectednonneuronal mammalian cell (i.e. a cell that does not naturally express any type of 5-HT or G-protein coupled receptor, thus will only express such a receptor if it is transfected into the cell) expressing a 5-HT$_{1F}$ receptor on its surface, or contacting a membrane preparation derived from such a transfected cell, with the ligand under conditions which are known to prevail, and thus to be associated with, in vivo binding of the ligands to a 5-HT$_{1F}$ receptor, detecting the presence of any of the ligand being tested bound to the 5-HT$_{1F}$ receptor on the surface of the cell, and thereby determining whether the ligand binds to, activates or prevents the activation of the 5-HT$_{1F}$ receptor. This response system is obtained by transfection of isolated DNA into a suitable host cell containing the desired second messenger system such as phosphoinositide hydrolysis, adenylate cyclase, guanylate cyclase or ion channels. Such a host system is isolated from pre-existing cell lines, or can be generated by inserting appropriate components of second messenger systems into existing cell lines. Such a transfection system provides a complete response system for investigation or assay of the activity of human 5-HT$_{1F}$ receptors with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of second messenger systems or their sequelae in transfection systems act as assays for binding affinity and efficacy in the activation of receptor function. A transfection system constitutes a "drug discovery system" useful for the identification of natural or synthetic compounds with potential for drug development that can be further modified or used directly as therapeutic compounds to activate or inhibit the natural functions of the human 5-HT$_{1F}$ receptor. The transfection system is also useful for determining the affinity and efficacy of known drugs at the human 5-HT$_{1F}$ receptor sites.

This invention also provides a method of screening drugs to identify drugs which specifically interact with, and bind to, the human 5-HT$_{1F}$ receptor on the surface of a cell which comprises contacting a mammalian cell comprising a DNA molecule encoding a human 5-HT$_{1F}$ receptor on the surface of a cell with a plurality of drugs, determining those drugs which bind to the mammalian cell, and thereby identifying drugs which specifically interact with, and bind to, the human 5-HT$_{1F}$ receptor. This invention also provides a method of screening drugs to identify drugs which interact with, and activate or block the activation of, the human 5-HT$_{1F}$ receptor on the surface of a cell which comprises contacting the mammalian cell comprising an isolated DNA molecule encoding and expressing a human 5-HT$_{1F}$ receptor with a plurality of drugs, determining those drugs which activate or block the activation of the receptor in the mammalian cell using a bioassay such as a second messenger assays, and thereby identifying drugs which specifically interact with, and activate or block the activation of, a human 5-HT$_{1F}$ receptor. The DNA in the cell may have a coding sequence substantially the same as the coding sequence shown in FIGS. 1A–1C (Seq. I.D. No. 1). Preferably, the mammalian cell is nonneuronal in origin. An example of a nonneuronal mammalian cell is an Ltk$^-$ cell, in particular the Ltk$^-$ cell designated L-5-HT$_{1F}$. Another example of a non-neuronal mammalian cell to be used for functional assays is a murine fibroblast cell line, specifically the NIH3T3 cell designated N-5-HT$_{1F}$. Drug candidates are identified by choosing chemical compounds which bind with high affinity to the expressed 5-HT$_{1F}$ receptor protein in transfected cells, using radioligand binding methods well known in the art, examples of which are shown in the binding assays described herein. Drug candidates are also screened for selectivity by identifying compounds which bind with high affinity to one particular 5-HT$_{1F}$ receptor subtype but do not bind with high affinity to any other serotonin receptor subtype or to any other known receptor site. Because selective, high affinity compounds interact primarily with the target 5-HT$_{1F}$ receptor site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

This invention provides a nucleic acid probe comprising a nucleic acid molecule of at least 15 nucleotides capable of specifically hybridizing with a sequence included within the sequence of a nucleic acid molecule encoding a human 5-HT$_{1F}$ receptor, for example with a coding sequence included within the sequence shown in FIGS. 1A–1C. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding human 5-HT$_{1F}$ receptors is useful as a diagnostic test for any disease process in which levels of expression of the corresponding 5-HT$_{1F}$ receptor is altered. DNA probe molecules are produced by insertion of a DNA molecule which encodes human 5-HT$_{1F}$ receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. An example of such DNA molecule is shown in FIGS. 1A–1C. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes human 5-HT$_{1F}$ receptor of are useful as probes for these genes, for their associated mRNA, or for the isolation of related genes by homology screening of genomic or cDNA libraries, or by the use of amplification techniques such as the Polymerase Chain Reaction. Synthesized oligonucleotides as described may also be used to determine the cellular localization of the mRNA produced by the 5-HT$_{1F}$ gene by in situ hybridization. An example of such an oligonucleotide is: 5'-TCTCACCACTCTCCAAAAG-GACTTGGCCATTCACCTCCTCCTTTG-3' (Seq. I.D. No. 9).

This invention also provides a method of detecting expression of a 5-HT$_{1F}$ receptor on the surface of a cell by detecting the presence of mRNA coding for a 5-HT$_{1F}$ receptor which comprises obtaining total mRNA from the cell using methods well known in the art and contacting the mRNA so obtained with a nucleic acid probe comprising a nucleic acid molecule of at least 15 nucleotides capable of specifically hybridizing with a sequence included within the sequence of a nucleic acid molecule encoding a human 5-HT$_{1F}$ receptor under hybridizing conditions, detecting the presence of mRNA hybridized to the probe, and thereby detecting the expression of the 5-HT$_{1F}$ receptor by the cell. Hybridization of probes to target nucleic acid molecules such as mRNA molecules employs techniques well known in the art. In one possible means of performing this method, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mRNA molecule which encodes a human 5-HT$_{1F}$ receptor so as to prevent translation of the mRNA molecule. The antisense oligonucleotide may have a sequence capable of binding specifically with any sequences of the cDNA molecule whose sequence is shown in FIGS. 1A–1C. As used herein, the phrase "binding specifically" means the ability of a nucleic acid sequence to recognize a nucleic acid sequence complementary to its own and to form double-helical segments through hydrogen bonding between complementary base pairs. A particular example of an antisense oligonucleotide is an antisense oligonucleotide comprising chemical analoguss of nucleotides.

This invention also provides a pharmaceutical composition comprising an amount of the oligonucleotide described above effective to reduce expression of a human 5-HT$_{1F}$ receptor by passing through a cell membrane and binding specifically with mRNA encoding a human 5-HT$_{1F}$ receptor in the cell so as to prevent its translation and a pharmaceutically acceptable hydrophobic carrier capable of passing through a cell membrane. The oligonucleotide may be coupled to a substance which inactivates mRNA, such as a ribozyme. The pharmaceutically acceptable hydrophobic carrier capable of passing through cell membranes may also comprise a structure which binds to a receptor specific for a selected cell type and is thereby taken up by cells of the selected cell type. The structure may be part of a protein known to bind a cell-type specific receptor, for example an insulin molecule, which would target pancreatic cells. DNA molecules having coding sequences substantially the same as the coding sequence shown in FIGS. 1A–1C may be used as the oligonucleotides of the pharmaceutical composition.

This invention also provides a method of treating abnormalities which are alleviated by reduction of expression of a 5-HT$_{1F}$ receptor which comprises administering to a subject an amount of the pharmaceutical composition described above effective to reduce expression of the 5-HT$_{1F}$ receptor by the subject. This invention further provides a method of treating an abnormal condition related to 5-HT$_{1F}$ receptor activity which comprises administering to a subject an amount of the pharmaceutical composition described above effective to reduce expression of the 5-HT$_{1F}$ receptor by the subject. Several examples of such abnormal conditions are dementia, Parkinson's disease, feeding disorders, pathological anxiety, schizophrenia, or a migraine headache.

Antisense oligonucleotide drugs inhibit translation of mRNA encoding these receptors. Synthetic oligonucleotides, or other antisense chemical structures are designed to bind to mRNA encoding the 5-HT$_{1F}$ receptor and inhibit translation of mRNA and are useful as drugs to inhibit expression of 5-HT$_{1F}$ receptor genes in patients. This invention provides a means to therapeutically alter levels of expression of human 5-HT$_{1F}$ receptors by the use of a synthetic antisense oligonucleotide drug (SAOD) which inhibits translation of mRNA encoding these receptors. Synthetic oligonucleotides, or other antisense chemical structures designed to recognize and selectively bind to mRNA, are constructed to be complementary to portions of the nucleotide sequences shown in FIGS. 1A–1C of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g. by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which binds and takes up the SAOD only within certain selected cell populations. For example, the SAOD may be designed to bind to a receptor found only in a certain cell type, as discussed above. The SAOD is also designed to recognize and selectively bind to the target mRNA sequence, which may correspond to a sequence contained within the sequence shown in FIGS. 1A–1C by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J.S. Cohen, Trends in Pharm. Sci. 10, 435 (1989); H.M. Weintraub, Sci. Am. January (1990) p. 40). In addition, coupling of ribozymes to antisense oligonucleotides is a promising strategy for inactivating target mRNA (N. Satvet et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce receptor expression in particular target cells of a patient, in any clinical condition which may benefit from reduced expression of $5\text{-HT}_{1F}$ receptors.

This invention provides an antibody directed to the human $5\text{-HT}_{1F}$ receptor, for example a monoclonal antibody directed to an epitope of a human $5\text{-HT}_{1F}$ receptor present on the surface of a cell and having an amino acid sequence substantially the same as an amino acid sequence for a cell surface epitope of the human $5\text{-HT}_{1F}$ receptor included in the amino acid sequence shown in FIGS. 1A–1C (Seq. I.D. Nos. 2, 7). Amino acid sequences may be analyzed by methods well known in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1A–1C will bind to a surface epitope of a human $5\text{-HT}_{1F}$ receptor, as described. Antibodies directed to human $5\text{-HT}_{1F}$ receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk− cells may be used as immunogens to raise such an antibody. Alternatively, synthetic peptides may be prepared using commercially available machines and the amino acid sequence shown in FIGS. 1A–1C. As a still further alternative, DNA, such as a cDNA or a fragment thereof, may be cloned and expressed and the resulting polypeptide recovered and used as an immunogen. These antibodies are useful to detect the presence of human $5\text{-HT}_{1F}$ receptors encoded by the isolated DNA, or to inhibit the function of the receptors in living animals, in humans, or in biological tissues or fluids isolated from animals or humans.

This invention provides a pharmaceutical composition which comprises an amount of an antibody directed to the human $5\text{-HT}_{1F}$ receptor effective to block binding of naturally occurring ligands to the $5\text{-HT}_{1F}$ receptor, and a pharmaceutically acceptable carrier. A monoclonal antibody directed to an epitope of a human $5\text{-HT}_{1F}$ receptor present on the surface of a cell and having an amino acid sequence substantially the same as an amino acid sequence for a cell surface epitope of the human $5\text{-HT}_{1F}$ receptor included in the amino acid sequence shown in FIGS. 1A–1C is useful for this purpose.

This invention also provides a method of treating abnormalities which are alleviated by reduction of expression of a human $5\text{-HT}_{1F}$ receptor which comprises administering to a subject an amount of the pharmaceutical composition described above effective to block binding of naturally occurring ligands to the $5\text{-HT}_{1F}$ receptor and thereby alleviate abnormalities resulting from overexpression of a human $5\text{-HT}_{1F}$ receptor. Binding of the antibody to the receptor prevents the receptor from functioning, thereby neutralizing the effects of overexpression. The monoclonal antibodies described above are both useful for this purpose. This invention additionally provides a method of treating an abnormal condition related to an excess of $5\text{-HT}_{1F}$ receptor activity which comprises administering to a subject an amount of the pharmaceutical composition described above effective to block binding of naturally occurring ligands to the $5\text{-HT}_{1F}$ receptor and thereby alleviate the abnormal condition. Some examples of abnormal conditions are dementia, Parkinson's disease, feeding disorders, pathological anxiety, schizophrenia, and a migraine headache.

This invention provides a method of detecting the presence of a $5\text{-HT}_{1F}$ receptor on the surface of a cell which comprises contacting the cell with an antibody directed to the human $5\text{-HT}_{1F}$ receptor, under conditions permitting binding of the antibody to the receptor, detecting the presence of the antibody bound to the cell, and thereby the presence of the human $5\text{-HT}_{1F}$ receptor on the surface of the cell. Such a method is useful for determining whether a given cell is defective in expression of $5\text{-HT}_{1F}$ receptors on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a human $5\text{-HT}_{1F}$ receptor. This invention also provides a transgenic nonhuman mammal expressing DNA encoding a human $5\text{-HT}_{1F}$ receptor so mutated as to be incapable of normal receptor activity, and not expressing native $5\text{-HT}_{1F}$ receptor. This invention also provides a transgenic nonhuman mammal whose genome comprises antisense DNA complementary to DNA encoding a human $5\text{-HT}_{1F}$ receptor so placed as to be transcribed into antisense mRNA which is complementary to mRNA encoding a $5\text{-HT}_{1F}$ receptor and which hybridizes tom RNA encoding a $5\text{-HT}_{1F}$ receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequence shown in FIGS. 1A–1C (Seq. I.D. No. 1). An example of a transgenic animal is a transgenic mouse. Examples of tissue specificity-determining regions are the metallothionein promotor (Low, M.J., Lechan, R.M., Hammer, R.E. et al. Science 231:1002–1004 (1986)) and the L7 promotor (Oberdick, J., Smeyne, R.J., Mann, J.R., Jackson, S. and Morgan, J.I. Science 248:223–226 (1990)).

Animal model systems which elucidate the physiological and behavioral roles of human 5-HT$_{1F}$ receptors are produced by creating transgenic animals in which the expression of a 5-HT$_{1F}$ receptor is either increased or decreased, or the amino acid sequence of the expressed 5-HT$_{1F}$ receptor protein is altered, by a variety of techniques. Examples of these techniques include: 1) Insertion of normal or mutant versions of DNA encoding a human 5-HT$_{1F}$ receptor or homologous animal versions of these genes, by microinjection, retrovital infection or other means well known to those skilled in the art, into appropriate fertilized embryos in order to produce a 5 transgenic animal (Hogan B. et al. Manipulating the Mouse Embryo, A Laboratory Manual, Cold Spring Harbor Laboratory (1986)). 2) Homologous recombination (Capecchi M.R. Science 244:1288–1292 (1989); Zimmer, A. and Gruss, P. Nature 338:150–153 (1989)) of mutant or normal, human or animal versions of these genes with the native gene locus in transgenic animals to alter the regulation of expression or the structure of these 5-HT$_{1F}$ receptors. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a human 5-HT$_{1F}$ receptor is purified from a vector (such as plasmid pMO5-h116a described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit the receptor, the transgenic animal model systems described above are useful for testing the biological activity of drugs directed against these 5-HT$_{1F}$ receptors even before such drugs become available. These animal model systems are useful for predicting or evaluating possible therapeutic applications of drugs which activate or inhibit these 5-HT$_{1F}$ receptors by inducing or inhibiting expression of the native or trans-gene and thus increasing or decreasing expression of normal or mutant 5-HT$_{1F}$ receptors in the living animal. Thus, a model system is produced in which the biological activity of drugs directed against these 5-HT$_{1F}$ receptors are evaluated before such drugs become available. The transgenic animals which over or under produce the 5-HT$_{1F}$ receptor indicate by their physiological state whether over or under production of the 5-HT$_{1F}$ receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to underexpression. Therefore, an animal which underexpresses receptor is useful as a test system to investigate whether the actions of such drugs which result in under expression are in fact therapeutic. Another use is that if overexpression is found to lead to abnormalities, then a drug which down-regulates or acts as an antagonist to 5-HT$_{1F}$ receptor is indicated as worth developing, and if a promising therapeutic application is uncovered by these animal model systems, activation or inhibition of the 5-HT$_{1F}$ receptor is achieved therapeutically either by producing agonist or antagonist drugs directed against these 5-HT$_{1F}$ receptors or by any method which increases or decreases the expression of these 5-HT$_{1F}$ receptors in man.

This invention provides a method of determining the physiological effects of expressing varying levels of human 5-HT$_{1F}$ receptors which comprises producing a transgenic nonhuman animal whose levels of human 5-HT$_{1F}$ receptor expression are varied by use of an inducible promoter which regulates human 5-HT$_{1F}$ receptor expression. This invention also provides a method of determining the physiological effects of expressing varying levels of human 5-HT$_{1F}$ receptors which comprises producing a panel of transgenic nonhuman animals each expressing a different amount of human 5-HT$_{1F}$ receptor. Such animals may be produced by introducing different amounts of DNA encoding a human 5-HT$_{1F}$ receptor into the ocytes from which the transgenic animals are developed.

This invention also provides a method for identifying a substance capable of alleviating abnormalities resulting from overexpression of a human 5-HT$_{1F}$ receptor comprising administering the substance to a transgenie nonhuman mammal expressing at least one artificially introduced DNA molecule encoding a human 5-HT$_{1F}$ receptor and determining whether the substance alleviates the physical and behavioral abnormalities displayed by the transgenic nonhuman mammal as a result of overexpression of a human 5-HT$_{1F}$ receptor. As used herein, the term "substance" means a compound or composition which may be natural, synthetic, or a product derived from screening. Examples of DNA molecules are DNA or cDNA molecules having a coding sequence substantially the same as the coding sequence shown in FIGS. 1A–1C.

This invention provides a pharmaceutical composition comprising an amount of the substance described supra effective to alleviate the abnormalities resulting from overexpression of 5-HT$_{1F}$ receptor and a pharmaceutically acceptable carrier.

This invention further provides a method for treating the abnormalities resulting from overexpression of a human 5-HT$_{1F}$ receptor which comprises administering to a subject an amount of the pharmaceutical composition described above effective to alleviate the abnormalities resulting from overexpression of a human 5-HT$_{1F}$ receptor.

This invention provides a method for identifying a substance capable of alleviating the abnormalities resulting from underexpression of a human 5-HT$_{1F}$ receptor comprising administering the substance to the transgenic nonhuman mammal described above which expresses only nonfunctional human 5-HT$_{1F}$ receptor and determining whether the substance alleviates the physical and behavioral abnormalities displayed by the transgenic nonhuman mammal as a result of underexpression of a human 5-HT$_{1F}$ receptor.

This invention also provides a pharmaceutical composition comprising an amount of a substance effective to alleviate abnormalities resulting from underexpression of 5-HT$_{1F}$ receptor and a pharmaceutically acceptable carrier.

This invention further provides a method for treating the abnormalities resulting from underexpression of a human 5-HT$_{1F}$ receptor which comprises administering to a subject an amount of the pharmaceutical composition described above effective to alleviate the abnormalities resulting from underexpression of a human 5-HT$_{1F}$ receptor.

This invention provides a method for diagnosing a predisposition to a disorder associated with the expression of a specific human 5-HT$_{1F}$ receptor allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a human 5-HT$_{1F}$ receptor and labelled with a detectable marker; e) detecting labelled bands which have hybridized to the DNA encoding a human 5-HT$_{1F}$ receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human 5-HT$_{1F}$ receptor allele.

This invention provides a method of preparing the isolated 5-HT$_{1F}$ receptor which comprises inducing cells to express 5-HT$_{1F}$ receptor, recovering the receptor from the resulting cells, and purifying the receptor so recovered. An example of an isolated 5-HT$_{1F}$ receptor is an isolated protein having substantially the same amino acid sequence as the amino acid sequence shown in FIGS. 1A–1C (Seq. I.D. Nos. 2, 7). For example, cells can be induced to express receptors by exposure to substances such as hormones. The cells can then be homogenized and the receptor isolated from the homogenate using an affinity column comprising, for example, serotonin or another substance which is known to bind to the receptor. The resulting fractions can then be purified by contacting them with an ion exchange column, and determining which fraction contains receptor activity or binds antireceptor antibodies.

This invention provides a method of preparing the isolated 5-HT$_{1F}$ receptor which comprises inserting nucleic acid encoding 5-HT$_{1F}$ receptor in a suitable vector, inserting the resulting vector in a suitable host cell, recovering the receptor produced by the resulting cell, and purifying the receptor so recovered. An example of an isolated 5-HT$_{1F}$ receptor is an isolated protein having substantially the same amino acid sequence as the amino acid sequence shown in FIGS. 1A–1C. This method for preparing 5-HT$_{1F}$ receptor uses recombinant DNA technology methods well known in the art. For example, isolated nucleic acid encoding 5-HT$_{1F}$ receptor is inserted in a suitable vector, such as an expression vector. A suitable host cell, such as a bacterial cell, or a eukaryotic cell such as a yeast cell, is transfected with the vector. 5-HT$_{1F}$ receptor is isolated from the culture medium by affinity purification or by chromatography or by other methods well known in the art.

This invention provides an antisense oligonucleotide having a sequence capable of binding specifically with any sequences of an mRNA molecule which encodes a receptor so as to prevent translation of the mRNA molecule (Seq. I.D. No. 9).

This invention also provides a transgenic nonhuman mammal expressing DNA encoding a receptor.

This invention further provides a transgenic nonhuman mammal expressing DNA encoding a receptor so mutated as to be incapable of normal receptor activity, and not expressing native receptor.

This invention provides a method of determining the physiological effects of expressing varying levels of a receptor which comprises producing a transgenic nonhuman animal whose levels of receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding the receptor with the ligand under conditions permitting binding of ligands known to bind to a receptor, detecting the presence of any of the ligand bound to the receptor, and thereby determining whether the ligand binds to the receptor.

Applicants have identified individual receptor subtype proteins and have described methods for the identification of pharmacological compounds for therapeutic treatments. Pharmacological compounds which are directed against specific receptor subtypes provide effective new therapies with minimal side effects.

This invention identifies for the first time a new receptor protein, its amino acid sequence, and its human gene. Furthermore, this invention describes a previously unrecognized group of receptors within the definition of a 5-HT$_{1F}$ receptor. The information and experimental tools provided by this discovery are useful to generate new therapeutic agents, and new therapeutic or diagnostic assays for this new receptor protein, its associated mRNA molecule or its associated genomic DNA. The information and experimental tools provided by this discovery will be useful to generate new therapeutic agents, and new therapeutic or diagnostic assays for this new receptor protein, its associated mRNA molecule, or its associated genomic DNA.

Specifically, this invention relates to the first isolation of a human cDNA and genomic clone encoding a 5-HT$_{1F}$ receptor. A new human gene for the receptor identified herein as 5-HT$_{1F}$ has been identified and characterized, and a series of related cDNA and genomic clones have been isolated. In addition, the human 5-HT$_{1F}$ receptor has been expressed in Ltk− cells and NIH3T3 cells by transfecting the cells with the plasmid pMO5-h116a. The pharmacological binding properties of the protein encoded have been determined, and these binding properties classify this protein as a serotonin 5-HT$_{1F}$ receptor. Mammalian cell lines expressing this human 5-HT$_{1F}$ receptor at the cell surface have been constructed, thus establishing the first well-defined, cultured cell lines with which to study this 5-HT$_{1F}$ receptor.

The invention will be better understood by reference to the experimental details which follow, but those skilled in the art will readily appreciate that the specific experiments detailed are only illustrative of the invention as described more fully in the claims which follow thereafter.

EXPERIMENTAL DETAILS

Materials and Methods

Polymerase Chain Reaction (PCR): The third (III) and fifth (V) transmembrane domains of the following receptors were aligned and used to synthesize a pair of "degenerate" primers: 5-HT$_{1A}$ (Seq. I.D. No. 3), 5-HT$_{1C}$ (Seq. I.D. No. 4), 5-HT$_2$ (Seq. I.D. No. 8) and the 5-HT$_{1D\alpha/\beta}$ (Seq. I.D. Nos. 5 and 6, respectively) receptors (patent pending). These primers hybridize to opposite strands of target sequences to allow amplification of the region between the corresponding transmembrane domains. That primer which was designed to anneal to transmembrane domain III is designated 3.17 and consists of a mixture of 192 different 31-mers with two inosine nucleotides; the primer which annealed to transmembrane domain V is designated 5.5 and consists of a mixture of 288 different 27-mers with five inosine nucleotides. EcoRI linkers were included at the 5' end of primer 3.17, to facilitate the subcloning of the amplified cDNA in pBluescript (Stratagene) vectors. 5 μg of poly (A+) RNA from rat brain was reverse transcribed by avian myeloblastosis virus reverse transcriptase (AMV) including 3 μM each of 3.17 and 5.5 primers. The resulting single-stranded cDNA was used in a PCR reaction under the following conditions: 94° C. for 1 minute, 50° C. for 2 minutes and 72° C. for 3 minutes for 40 cycles. Following PCR, 90 μl of the reaction was phenol:chloroform extracted and precipitated; 10 μl was visualized on a gel using ethidium bromide staining. After precipitation the sample was treated with T4 DNA polymerass and digested with EcoR1 prior to separation on a 1% agarose gel. The DNA fragment was isolated from the gel, kinased and cloned into pBluescript. Recombinant clones were analyzed by sequencing.

Cloning and Sequencing: A human lymphocyte genomic library (Stratagene) was screened using the rat S51 fragment (obtained by PCR) as a probe. The probe was labeled with $^{32}$p by the method of random priming (Feinberg et al., 1983). Hybridization was performed at 50° C. in a solution containing 50% formamide, 10% dextran sulfate, 5× SSC (1× SSC is 0.15 M sodium chloride, 0.015 M sodium citrate), 1× Denhardt's (0.02% polyvinylpyrrolidone, 0.02% Ficoll, and 0.02% bovine serum albumin), and 200 μg/ml of sonicated salmon sperm DNA. The filters were washed at 50° C. in 0.1× SSC containing 0.1% sodium dodecyl sulfate (SDS) and exposed at −70° C. to Kodak XAR film in the presence of an intensifying screen. Lambda phage hybridizing to the probe were plaque purified and DNA was prepared for southern blot analysis (Southern, 1975; Maniatis et al., 1982). For subcloning and further Southern blot analysis DNA was inserted into pUC18 (Pharmacia, Piscataway, N.J.). Nucleotide sequence analysis was done by the Sanger dideoxy nucleotide chain-termination method (Sanger 1977) on denatured double-stranded plasmid templates using Sequenase (U.S. Biochemical Corp., Cleveland, Ohio).

Expression: The entire coding region of clone h116a was cloned into the eukaryotic expression vector pcEXV-3 (Miller, 1986). Stable cell lines were obtained by cotransfection with the plasmid pcEXV-3 (containing the 5-HT$_{1F}$ receptor gene) and the plasmid pGCcos3neo (containing the aminoglycoside transferase gene) into Ltk− cells or NIH3T3 cells using calcium phosphate (reagents obtained from Specialty Media, Lavellette, NJ). The cells were grown in a controlled environment (37° C., 5% CO$_2$) as monolayers in Dulbecco's modified Eagle medium (Gibco, Grand Island, N.Y.) containing 25 mMglucose and supplemented with 10% bovine calf serum, 100 U/ml penicillin G and 100 μg/ml streptomycin sulfate. Stable clones were then selected for resistance to the antibiotic G-418 and harvested membranes were screened for their ability to bind [$^3$H]serotonin.

Membrane Preparation: Membranes were prepared from transfected Ltk- cells which were grown to 100% confluency. The cells were washed twice with phosphate-buffered saline, scraped from the culture dishes into 5 ml of ice-cold phosphate-buffered saline, and centrifuged at 200 × g for 5 min at 4°. The pellet was resuspended in 2.5 ml of ice-cold Tris buffer (20 mM Tris -HCl, pH 7.4 at 23°, 5 mM EDTA) and homogenized by a Wheaton tissue grinder. The lysate was subsequently centrifuged at 200 × g for 5 min at 4° to pellet large fragments which were discarded. The supernatant was collected and centrifuged at 40,000 × g for 20 min at 4°. The pellet resulting from this centrifugation was washed once in ice-cold Tris wash buffer and finally resuspended in a final buffer containing 50 mM Tris-HCl and 0.5 mM EDTA, pH 7.4 at 23°. Membrane preparations were kept on ice and utilized within two hours for the radioligand binding assays. Protein concentrations were determined by the method of Bradford (1976) using bovine serum album-in as the standard.

Radioligand Binding: [$^3$H]5HT binding was performed using slight modifications of the 5-HT$_{1D}$ assay conditions reported by Herrick-Davis and Titeler (1988) with the omission of masking ligands. Radioligand binding studies were achieved at 37° C. in a total volume of 250 μl of buffer (50 mM Tris, 10 mM MgCl$_2$, 0.2 mM EDTA, 10 μM pargyline, 0.1% ascorbate, pH 7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 10–12 concentrations of compound. Incubation times were 30 min for both saturation and displacement studies based upon initial investigations which determined equilibrium binding conditions. Nonspecific binding was defined in the presence of 10 μM 5-HT. Binding was initiated by the addition of 50 μl membrane homogenates (10–20 μg). The reaction was terminated by rapid filtration through presoaked (0.5% polyethyleneimine) filters using 48R Cell Brandel Harvester (Gaithersburg, MD). Subsequently, filters were washed for 5 sec with ice cold buffer (50mM Tris HCL, pH 7.4 at 4° C.), dried and placed into vials containing 2.5 ml of Readi-Safe (Beckman, Fullerton, CA) and radioactivity was measured using a Beck/nan LS 5000TA liquid scintillation counter. The efficiency of counting of [$^3$H]5HT averaged between 45–50%. Binding data was analyzed by computer-assisted nonlinear regression analysis (Accufit and Accucomp, Lundon Software, Chagrin Falls, OH). IC$_{50}$ values were converted to K$_i$ values using the Cheng-Prusoff equation (1973). All experiments were performed in triplicate.

Measurement of cAMP Formation

Transfected NIH3T3 cells (estimated Bmax from one point competition studies = 488 fmol/mg of protein) were incubated in DMEM, 5 mM theophylline, 10 mM Hepes (4-[2-Hydroxyethyl]-1-piperazineethanesulfonic acid), 10 μM pargyline, for 20 minutes at 37° C., 5% CO2. Drug doseeffect curves were then conducted by adding 6 different final concentrations of drug, followed immediately by the addition of forskolin (10 μM). Subsequently, the cells were incubated for an additional 10 minutes at 37° C., 5% CO2. The media was aspirated and the reaction terminated by the addition of 100mM HCl. The plates were stored at 4° C. for 15 minutes and centrifuged for 5 minutes (500 × g at 4° C.) to pellet cellular debris. Aliquots of the supernatant fraction were then stored at −20° C. prior to assessment of cAMP formation by radioimmunoassay (cAMP Radioimmunoassay kit, Advanced Magnetics, Cambridge, MA).

Drugs: [$^3$H]5-HT (specific activity = 28 Ci/mmole) was obtained from New England Nuclear, Boston, MA. All other chemicals were obtained from commercial sources and were of the highest grade purity available.

Results

Cloning of a Novel Gene Encoding a 5HT$_{1F}$ Receptor

Polyadenylated (poly A+) RNA prepared from rat brain was reverse transcribed and the resulting cDNAs were subjected to amplification by PCR with the use of a set of "degenerate" primers. The synthesis of these primers were based on sequences corresponding to the third and fifth transmembrane segments of the current set of available serotonin receptors. The primers were designed to amplify only serotonin specific sequences. This was accomplished, particularly with the transmembrane domain V primer, which was designed to anneal at its 3' end only to the sequence "AFY(F)IP". We have determined by sequence analysis that the presence of an alanine (A) rather than a setins (S) in the position immediately amine-terminal to the sequence "FY(F)IP" is an amine acid which can distinguish the closely related adrenergic and dopaminergic receptor families from the serotonergic receptor family. After 30 amplification cycles, agarose gel electrophoresis revealed a clear pattern of cDNA species of approximately 250 base pairs. Individual cDNAs were cloned directly into pBluescript and subjected to sequence analysis. One clone, designated S51, was observed to encode a novel serotonin receptor. We then screened a human genomic placental library with the PCR fragment S51. Isolation of the full-length coding region was obtained from a genomic clone designated h116a.

Nucleotide Sequence and Deduced Amine Acid Sequence of h116a

DNA sequence information obtained from clone h116a is shown in FIGS. 1A–1C. An open reading frame extending from an ATG start codon at position 1 to a stop codon at position 1098 can encode a protein 366 amino acids in length, having a relative molecular mass (M$_r$) of 41,660. A comparison of this protein sequence with previously characterized neurotransmitter receptors indicates that h116a encodes a receptor which is a new member of a family of molecules which span the lipid bilayer seven times and couple to guanine nucleotide regulatory proteins (the G protein-coupled receptor family). A variety of structural features which are invariant in this family were present including the aspattic acid residues of transmembrane regions II and III, the DRY sequence at the end of transmembrane region III, and the conserved proline residues of transmembrane regions IV, V, VI and VII (Hartig et al. and references therein), were present in clone h116a. A comparison of the transmembrane homology of h116a to the other cloned serotonin receptors is shown if FIGS. 2A–2D exhibits the following order of identity: 5-HT$_{1D\alpha}$(61%), 5-HT$_{1D\beta}$(59%), 5-HT$_{1A}$ (54%), 5-HT$_{1C}$ (44%) and 5-HT$_{1D\beta}$(44%).

Receptor Expression in Transfected Mammalian Cells

Saturation analysis of membranes prepared from stably transfected Ltk− cells demonstrated that the receptor expressed was saturable and of high affinity. Scatchard plot analysis by non-linear regression revealed a Kd of 9.2 ± 0.99 nM (mean ± S.E.M., n=4) and a B$_{max}$4.4 ± 0.36 picomoles / mg of protein (mean ± S.E.M., n=4). The percent specific binding determined at the measured Kd value for [$^3$H]5-HT was greater than 85% of total binding. Furthermore, evidence that the receptor is coupled to a G-protein was demonstrated by the ability of Gpp(NH)p, a non-hydrolyzable analog Of GTP, to inhibit the specific binding of [$^3$H]5-HT (IC$_{50}$ = 243 ± 115, n$_H$ = 0.71 ± 0.08, I$_{max}$ = 55.6 ± 3.2% ; mean ± S.E.M., n=3). Additional data demonstrating that this coupling to a G-protein is functionally relevant is provided below.

Pharmacological analysis of the receptor was accomplished by testing the ability of drugs from different chemical classes to displace [3H]5-HT specific binding (Table 1). Of the compounds investigated, 5-HT possessed the highest affinity which according to the classification system of Peroutka and Snyder (1979) makes this site a member of the 5-HT$_1$ class. Interestingly, 5-CT possessed low affinity and, thus, discriminates this receptor from that of the 5-HT$_{1D}$ receptor as well as other members of this class. The one exception appears to be the recently cloned 5-HT$_{1E}$ receptor which also has low affinity for 5-CT. Various ergoline compounds also bound with high affinity including methylergonovine and methysergide. Excluding 1-napthylpiperazine (Ki = 54), piperazine derivatives had low affinity. Interestingly, the rauwolfia alkaloids, rauwolscine and yohimbine, which are alpha-2 adrenergic antagonists had fair affinity for this serotonergic receptor. Furthermore, miscellaneous serotonergic agents that possess high affinity for various receptors within the serotonin family including ketanserin (5-HT$_2$), 8-OH-DPAT (5-HT$_{1A}$), DOI (5-HT$_{1C}$/5-HT$_2$), spiperone (5-HT$_{1A}$/5-HT$_2$), pindolol (5-HT$_{1A}$/5-HT$_{1B}$) and zacopride (5-HT$_3$) had very poor affinity. Taken together, the pharmacological profile of the 5-HT$_{1F}$ receptor is unique and contrasts to that of other known serotonin receptors. Accordingly, the probability of developing selective drugs for this receptor subtype is increased.

TABLE 1

Ki (nM) values of various drugs for the inhibition of [$^3$H]5-HT specific binding to clonal 5-HT$_{1F}$ cell membranes. Binding assays were performed with 4.5–5.5 nM of [$^3$H]5-HT and 10–12 different concentrations of each inhibitory drug. Ki values were calculated from the IC$_{50}$ values using the Cheng-Prusoff equation. Each value is the mean ± S.E.M. of 2–4 independent determinations.

| COMPOUND | Ki (nM) |
|---|---|
| 5-HT | 10.3 ± 2.0 |
| Sumatriptan | 23.0 ± 11.0 |
| Ergonovine | 31.0 ± 1.5 |
| Methylergonovine | 31.0 ± 11.0 |
| Methysergide | 34.0 ± 4.9 |
| 5-Methoxy-N,N-DMT | 37.5 ± 1.5 |
| 1-Napthylpiperazine | 54.0 ± 3.8 |
| Yohimbine | 92.0 ± 11.0 |
| Ergotamine | 171 ± 28 |
| α-Methyl-5-HT | 184 ± 35 |
| NAN 190 | 203 ± 13 |
| Dihydroergotamine | 276 ± 49 |
| Metergoline | 341 ± 71 |
| 2-Methyl-5-HT | 413 ± 5.6 |
| Methiothepin | 652 ± 41 |
| 5-CT | 717 ± 71 |
| TFMPP | 1,0002 ± 85 |
| 5-MT | 1,166 ± 197 |
| SCH 23390 | 1,492 ± 165 |
| 5-Benzoxytryptamine | 1,495 ± 893 |
| DP-5-CT | 1,613 ± 817 |
| DOI | 1,739 ± 84 |
| 8-OH-DPAT | 1,772 ± 38 |
| 5-Fluorotryptamine | 1,805 ± 220 |
| mCPP | 2,020 ± 36 |
| Tryptamine | 2,409 ± 103 |
| Quipazine | 4,668 ± 814 |
| Ritanserin | 3,521 ± 86 |
| Propanolol | 8,706 ± 97 |
| Ketanserin | >10,000 |
| Spiperone | >10,000 |
| Zacopride | >10,000 |
| Pindolol | >10,000 |
| Mesulergine | >10,000 |
| Harmaline | >10,000 |
| Melatonin | >10,000 | cAMP Assay

Additional supporting evidence that the 5-HT1F receptor is functionally coupled to a G-protein was obtained by testing the ability of 5-HT as well as other representative serotonergic drugs to inhibit forskolin stimulated cAMP production in NIH3T3 cells transfected with the 5-HT1F receptor. The endogenous indoleamine, 5-HT, produced a concentration-related decrease in forskolin-stimulated cAMP production with an EC50 of 7.1 ± 1.3 nM (n = 4). The maximum inhibition of cAMP production by 5-HT was 67 ± 5.4%. Additionally, the serotonergic compounds 1-napthylpiperazine and lysergol inhibited forskolin-stimulated cAMP production with EC50 values of 4.5 ± 0.2 nM and 8.8 ± 4.3 nM (n = 2), respectively.

Discussion

The deduced amino acid sequence of h116a was analyzed to uncover relationships between it and the other cloned serotonin receptor sequences. Although the homology within the membrane spanning domains was greatest with the 5-HT$_{1D}$ receptor (FIG. 2), the nature of this newly cloned receptor could not be clearly predicted. The rational for this ambiguity is the interpretation of the transmembrane domain homology (approximately 60%) to the 5-HT$_{1D\beta}$ and 5-HT$_{1D\beta}$ receptor subfamily. Closely related members of a "subfamily" of serotonin receptors (i.e. "subtypes") generally share a common transmitter and also have similar pharmacological profiles and physiological roles (for example, 5-HT$_2$ and 5-HT$_{1C}$ or 5-HT$_{1D\beta}$ and 5-HT$_{1D\beta}$). Such "subtypes" display an amino acid identity of approximately 75–80% in their transmembrane domains. Serotonin receptors which are not members of the same "subfamily", but are members of the serotonin "family" (in which the receptors use the same neurotransmitter; i.e. 5-HT$_2$ and 5-HT$_{1D\beta}$) generally show much lower transmembrane homology (approximately 45%). Such transmembrane amino acid homologies can, therefore, give insight into the relationship between receptors and be used as predictors of receptor pharmacology. According to this type of analysis, although the newly cloned receptor appears to be more related to the 5-HT$_{1D}$ subfamily, it is likely to be in a subfamily distinct from all the other serotonin receptors. Interestingly, the transmembrane homology between the 5HT$_{1E}$ and 5HT$_{1F}$ receptors is 72%. It is therefore possible that these receptors may be "subtypes", rather than members of distinct "subfamilies".

The present pharmacological evidence substantiates the existence of a novel serotonin receptor in the human brain and peripheral tissues. Comparison of the binding affinities for various drugs observed in native membranes for other known serotonergic receptors (see Hoyer, 1989) to that of the 5-HT$_{1F}$ receptor demonstrates that the pharmacological profile does not fit any known receptor to date. The cloning of the 5-HT$_{1F}$ site will now allow more extensive investigations into the nature of this unique serotonergic receptor.

The structure-activity relationships observed in the present study suggest that there are important requirements for high affinity binding to the 5-HT$_{1F}$ receptor. Substitution or removal of the 5-hydroxy group on serotonin significantly decreases the affinity for the receptor (egs., tryptamine, 5-methoxytryptamine and 5-carboxyamidotryptamine). Additionally, α-methylation and 2-methylation of 5-HT lowers its affinity by 20 and 40 fold, respectively, for the 5-HT$_{1F}$ site. In contrast to these substitutions, N,N-dimethylation of the aliphatic side chain of the indole ring increases the affinity approximately 20 fold (unpublished observations)Interestingly, 5-methoxy-N,N-dimethyltryptamine which possesses both a 5-hydroxy substitution as well as a N,N-dimethylation has an affinity much higher than the other 5-substituted tryptamine derivatives. Basic structural requirements of the ergoline derivatives demonstrate that N-methylation of the indole ring does not decrease affinity as does bulky substitutions. Furthermore, piperazine derivatives are not bound at high affinity.

Notably, the application of the human 5-HT$_{1F}$ receptor clone to pharmaceutical research can lead to new drug design and development. In this regard, it is important to point out that the affinities of sumatriptan, methylergonovine and methysergide for this receptor suggest that this site may be involved in the control of migraine headaches. Certainly, these compounds have had success in the clinic for the treatment of this debilitating disorder (Sleight et al., 1990). Notably, however, it has been thought that the action of these compounds is mediated at 5-HT$_{1D}$ receptors for sumatriptan and 5-HT$_2$ receptors for methysergide. Interestingly, methylergonovine may be an active metabolite of methysergide which can be responsible for some of the therapeutic antimigraine effects of methysergide. This novel site with affinity for these agents would now suggest that there is one serotonergic receptor which may be responsible for both the pathogenesis and, accordingly, the pharmacological treatment. Importantly, the agents prescribed for migraine are not selective for any one particular serotonin receptor and, thus, the. physiological significance of drugs acting at one specific site remains controversial (Humphrey P.P.A. et al., 1990). The notion that the 5-HT$_{1F}$ receptor is involved in migraine may be supported by evidence demonstrating that metergoline which has high affinity for the 5-HT$_{1D}$ receptor does not block the effects of sumatriptan in the dog saphenous vein (Sumner and Humphrey, 1990) inferring that this vascular model may contain the novel 5-HT$_{1F}$ site. Furthermore, this data can support the idea that sumatriptan acts at 5-HT$_{1F}$ receptors as an antimigraine drug. The potential of the 5-HT$_{1F}$ receptor as a novel target for migraine where selective drugs may be developed is an exciting possibility which needs to be explored.

Another consideration for therapeutic application of this site may be related to the treatment of feeding disorders such as obesity, bulimea nervosa and/or anorexia nervosa. The involvement of serotonin and feeding behavior has received much attention during the last decade. It is now known that many of the identified and well-characterized serotonergic receptors are capable of modulating feeding (Blundell and Lawton, 1990). Notably, serotonin uptake blockers which have been used to treat feeding disorders act nonselectively and as such have side-effect potential (Jimerson et al., 1990). The fact that the 5-HT$_{1F}$ receptor has been cloned from both peripheral and central sites suggests from an anatomical standpoint that it can be found in strategic locations where feeding may be altered. Although many different serotonergic receptors are involved in feeding, the search for the one site that can be exploited for selective drug development has yet to be found. There is no doubt that interest exists in finding drugs that interact with the serotonin system for the treatment of feeding disorders (Cooper, 1989).

Overall, the 5-HT$_{1F}$ receptor can be an important site stimulated by nonselectively blocking serotonin uptake as is accomplished with certain antidepressants. In regard to this, serotonin uptake blockers are effective in treating neuropsychiatric disorders such as depression and obsessive-compulsive illness (Asberg et al., 1986; Sleight et al., 1990; Insel et al., 1985). However, these agents have side effects and, in fact, the mechanism of action for these compounds are not linked to any particular serotonergic receptor. The possibility that agents selective for the 5-HT$_{1F}$ receptor may have clinical utility as antidepressants, for example, without the side effects attributed to current treatment modalities can have significant implications for drug therapy.

In summary, the pharmacological profile of the cloned human 5-HT$_{1F}$ receptor is unique and contrasts to other known serotonergic receptors. The utility of this site expressed in a cellular system and, thus, isolated for study will create excellent opportunities in drug development directed towards a novel serotonergic receptor that may have wide-range implications for drug therapy. Ultimately, indepth investigations into the localization of this receptor in brain and peripheral tissue will target new sites that may lead to functional roles of the serotonergic receptor. Indeed, the potential therapeutic applications may extend to neuropsychiatric disorders including depression, anxiety, schizophrenia, dementia and obsessive-compulsive illness as well as obesity and migraine.

Additionally, the localization of the 5-HT$_{1F}$ receptor in the spinal cord will suggest a possible role in modulation of nonreceptive stimuli which may lead to analgesic drug development. Furthermore, the presence of the 5-HT1F on vascular tissue may deem this site useful for cardiovascular drug applications.

References

Asberg, M., Eriksson, B., Matensson, B., Traskman-Bendz, L. and Wagner, A.: Therapeutic effects of serotonin uptake inhibitors in depression. J. Clin. Psychiat. 47:23–35, 1986.

Bradford, M.: A rapid and sensitive method for the quantification of microgram quantities of protein utilizing the principle of protein-dye binding. Anal. Biochem. 72:248–254, 1976.

Blundell, J.E. and Lawton, C.L.: Serotonin receptor subtypes and the organisation of feeding behaviour: Experimental models. In: Serotonin: From cell biology to pharmacology and therapeutics. (eds. Paoletti, R., Vanhoutte, P.M., Brunello, N. and Maggi, F.M.) Boston:Kluwer Academic Publishers, pp 213–219, 1990.

Branchek, T., Weinshank, R.L., Macchi, M.J., Zgombick, J.M. and Hartig, P.R.: Cloning and expression of a human 5-HT1D receptor. The Second IUPHAR Satellite Meeting on Serotonin, Basel, Switzerland, Jul. 11–13, 1990, Abstract # 2.

Cheng, Y.C. and Prusoff, W.H.: Relationship between the inhibition constant (Ki) and the concentration of inhibitor which causes 50% inhibition (IC50) of an enzyme reaction. Biochem. Pharmacol. 22:3099–3108, 1973.

Cooper, S.J.: Drugs interacting with 5-HT systems show promise for treatment of eating disorders. TIPS 10:56–57, 1989.

Fargin, A., Raymond, J.R., Lohse, M.J., Kobilka, B.K. Caron, M.G. and Lefkowitz, R.J.: The genomic clone G-21 which resembles a $\beta$-adrenergic receptor sequence encodes the 5-HT1A receptor. Nature 335: 358–360, 1988.

Feinberg, A.P., and Vogelstein, B. A technique for radiolabeling DNA restriction endonuclease fragments to high specific activity. Anal. Biochem. 132:6–13, 1983.

Gaddum, J.H. and Picarelli, Z.P.: Two kinds of tryptamine receptor. Brit. J. Pharmacol. 12:323–328, 1957.

Glennon, R.A.: Serotonin receptors: Clinical implications. Neurosci. Biobehav. Rev. 14:35–47, 1990.

Green, A.R.: Neuropharmacology of serotonin. Oxford:. Oxford University Press, 1985.

Hamon, M., Lanfumey, L., El Mestikawy, S., Boni, C., Miquel, M.-C., Bolanos, F., Schechter, L. and Gozlan, H.: The main features of central 5-HT1 receptors. Neuropsychopharmacol. 3(5/6):349–360, 1990.

Hartig, P.R., Kao, H.-T., Macchi, M., Adham, N., Zgombick, J., Weinshank, R. and Branchek, T.: The molecular biology of serotonin receptors: An overview. Neuropsychopharmacol. 3(5/6):335–347, 1990.

Herrick-Davis K. and Titeler, M.: Detection and characterization of the serotonin 5-HT$_{1D}$ receptor in rat and human brain. J. Neurochem. 50:1624–1631, 1988.

Hoyer, D.: Biochemical mechanisms of 5-HT receptor-effector coupling in peripheral tissues. In: Peripheral actions of 5-HT. (ed. Fozard, J.R.) Oxford:Oxford University Press, pp 72–99, 1989.

Humphrey, P.P.A., Feniuk, W., Perten, M.J., Beresford, I.J.M., Skingle, M. and Whalley, E.T.: Serotonin and migraine. Ann. N.Y. Acad. Sci. 600:587–600, 1990.

Insel, T.R., Mueller, E.A., Alterman, I., Linnoila, M. and Murphy, D.L.: obsessive-compulsive disorder and serotonin: Is there a connection? Biol. Psychiat. 20:1174–1188, 1985.

Jimerson, D.C., Lesem, M.D., Hegg, A.P. and Brewerton, T.D.: Serotonin in human eating disorders. Ann. N.Y. Acad. Sci. 600:532–544, 1990.

Julius, D., MacDermott, A.B., Axel, R. and Jessell, T.M.: Molecular characterization of a functional cDNA encoding the serotonin 1C receptor. Science 241:558–564, 1988.

Leonhardt, S., Herrick-Davis, K. and Titeler, M.: Detection of a novel serotonin receptor subtype (5-HT1F) in human brain: Interaction with a GTP-binding protein. J. Neurochem. 53(2):465–471, 1989.

Maniatis, T., Fritsch, E.F., and Sambrook, J. Molecular Cloning: A Laboratory Manual, Cold Spring Harbor Laboratory, Cold Spring Harbor, New York, 1982.

Osborne, N.N. and Hamon, M.: Neuronal serotonin. Chichester: John Wiley and Sons, Inc., 1988.

Peroutka, S.J.: Serotonin receptor subtypes: Basic and clinical aspects. New York: Wiley-Liss, Inc., 1991.

Peroutka, S. J. and Snyder, S. H.: Multiple serotonin receptors, differential binding of [$^3$H]5-hydroxytryptamine, [$^3$H]lysergic acid diethylamide and [$^3$H]spiroperidol. Mol. Pharmacol. 16: 687–699, 1979.

Pritchett, D.B., Bach, A.W.J., Wozny, M., Taleb, O., Dal Toso, R., Shih, J. and Seeburg, P.H.: Structure and functional expression of cloned rat serotonin 5-HT2 receptor. EMBO J. 7:4135–4140, 1988.

Rapport, M.M., Green, A.A. and Page, I.H.: Purification of the the substance which is responsible for vasoconstrictor activity of serum. Fed. Proc. 6:184, 1947.

Rapport, M.M.: Serum vasoconstrictor (serotonin) V. Presence of creatinine in the complex. A proposed structure of the vasoconstrictor principle. J. Biol. Chem. 180:961–969, 1949.

Sanders-Bush, E.: The Serotonin Receptors. Clifton, New. Jersey: Humana Press, 1988.

Sleight, A.J., Pierce, P.A., Schmidt, A.W., Hekmatpanah, C.R. and Peroutka, S.J.: The clinical utility of serotonin receptor active agents in neuropsychiatric disease. In: Serotonin receptor subtypes: Basic and clinical aspects. (ed. Peroutka, S.J.) New York:Wiley-Liss, Inc., pp 211–227, 1990.

Sumner, M.J. and Humphrey, P.P.A.: Sumatriptan (GR43175) inhibits cyclic-AMP accumulation in dog isolated saphenous vein. Br. J. Pharmacol. 99:219–220, 1990.

---

What is claimed is:

1. An isolated nucleic acid molecule encoding a human 5-HT$_{1F}$ receptor having the coding sequence shown in FIGS. 1A–1C.

2. A vector comprising the DNA molecule of claim 1.

3. A vector comprising the vector of claim 2.

4. A plasmid of claim 3 which further comprises mammalian regulatory elements operably linked to the DNA encoding the human b 5-HT$_{1F}$ receptor.

5. A mammalian cell comprising the plasmid of claim 3.

6. An Ltk⁻ cell comprising the plasmid of claim 3.

7. An NIH3T3 cell comprising the plasmid of claim 3.

8. A vector of claim 2 which further comprises bacterial regulatory elements operably linked to the DNA encoding the human 5-HT$_{1F}$ receptor.

9. A vector of claim 2 which further comprises yeast regulatory elements operably linked to the DNA encoding the human 5-HT$_{1F}$ receptor.

10. A vector of claim 2 which further comprises mammalian regulatory elements operably linked to the DNA encoding the human 5-HT$_{1F}$ receptor.

11. A plasmid comprising the cDNA molecule of claim 1 which further comprises mammalian regulatory elements operably linked to the cDNA, which is pMO5-h116a.

12. An Ltk⁻ cell comprising the plasmid of claim 11, which is L-5-HT$_{1F}$.

13. An NIH3T3 cell comprising the plasmid of claim 11, which is N-5-HT$_{1F}$.

* * * * *

UNITED STATES PATENT AND TRADEMARK OFFICE
CERTIFICATE OF CORRECTION

PATENT NO. : 5,360,735
DATED : November 1, 1994
INVENTOR(S) : Richard L. Weinshank, et al.

It is certified that error appears in the above-indentified patent and that said Letters Patent is hereby corrected as shown below:

column 1, lines 49-50 "$5\text{-}HT_{1F}$" should read --$5\text{-}HT_{1E}$--.

column 5, line 15, "$5\text{-}HT_{1F}$" should read --$5\text{-}HT_{1A}$--.

column 6, line 53, "pUC1S" should read --pUC18--.

column 8, line 48, "and thereby determining lo whether" should read --and thereby determining whether--.

column 15, line 10, "retrovital" should read --retroviral--.

column 15, line 13, "produce a 5 transgenic animal" should read --produce a transgenic animal--.

column 16, line 51, "transgenie" should read --transgenic--.

column 21, line 36, "doseeffect" should read --dose-effect--.

column 22, line 1, "setins" should read --serine--.

column 22, line 30, "aspattic" should read --aspartic--.

column 23, in Table 1, "1,0002" should read --1,002--.

column 24, line 16, "common transmitter and also 15 have similar" should read --common transmitter and also have similar--.

column 24, line 32, "30 from all the other serotonin receptors." should read --from all the other serotonin receptors.--.

UNITED STATES PATENT AND TRADEMARK OFFICE
CERTIFICATE OF CORRECTION

PATENT NO. : 5,360,735
DATED : November 1, 1994
INVENTOR(S) : Richard L. Weinshank It is certified that error appears in the above-indentified patent and that said Letters Patent is hereby corrected as shown below:

column 49, claim 3, "A vector comprising the vector of claim 2" should read --A plasmid comprising the vector of claim 2--.

column 49, claim 4, "DNA encoding the human b 5-$HT_{1F}$ receptor" should read --DNA encoding the human 5-$HT_{1F}$ receptor.--.

Signed and Sealed this

Third Day of October, 1995

*Attest:*

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1730 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( v i i ) IMMEDIATE SOURCE:
        ( A ) LIBRARY: human lymphocyte genomic
        ( B ) CLONE: hl16a ( i x ) FEATURE:
        ( A ) NAME/KEY: CDS
        ( B ) LOCATION: 616..1713

( i x ) FEATURE:
        ( A ) NAME/KEY: matpeptide
        ( B ) LOCATION: 616..1713

( x i ) SEQUENCE DESCRIPTION: SEQ ID NO:1:

```
TTGCATGCCT GCAGGTCGAC TCTAGAGGAT CCCCGGGTAC CGAGCTCGAA TTCCTTTGTT        60
```

-continued

| | | | | |
|---|---|---|---|---|
| ATTTTGTCAT | GCTTCAAGCC | TAGGAAAAGC | CTAAGCAAAA | CTCTTGGTGG GCTCTTTGTT | 120 |
| ACATTCCAGC | CTTTGAATAA | GGGCACTGGC | TCTATCAGCT | TTGAATATAT AACTCAACTA | 180 |
| GTCAGTCAGT | AGTACTGAAA | CAGTTGTTAC | GGAGGCCTGC | GTTATTGAGA TCGGGCCTGC | 240 |
| CACACTTTTA | AACTTTTCT | GACATGGACA | AAGAGAAAAA | CCAATTCTAT AATGGCAGAG | 300 |
| ATTTCACTGA | GTAACAAGCT | AGAGTATCAT | TAAAATTGT | TGTATTTAAC CTATATTTTA | 360 |
| AGAAATGTTT | TGGAAGTTAC | TGGCTTTTTT | TACTGTTCTC | ATTAAATTTC TTAAATAAAA | 420 |
| AGGAAAACTA | AAACCTTCAA | TCTGAACCTC | ATTTTTTAA | TCTATAGAAT ATTCTGGGTA | 480 |
| AACATAACAT | ACACTTTTA | AAAATTATTC | TGAAGGAAG | AGAAAAGTTC TTGAAGCCTT | 540 |
| CTCTGAACTG | TTTTTCTCT | TCCCTTGTTA | CAGGTATCCA | TTTTCAGCT ATATTAATCT | 600 |
| TTTAAAACAA | AGAAA | | | | |

ATG GAT TTC TTA AAT TCA TCT GAT CAA AAC TTG ACC  651
Met Asp Phe Leu Asn Ser Ser Asp Gln Asn Leu Thr
 1           5                    10

TCA GAG GAA CTG TTA AAC AGA ATG CCA TCC AAA ATT CTG GTG TCC CTC  699
Ser Glu Glu Leu Leu Asn Arg Met Pro Ser Lys Ile Leu Val Ser Leu
         15                   20                  25

ACT CTG TCT GGG CTG GCA CTG ATG ACA ACA ACT ATC AAC TCC CTT GTG  747
Thr Leu Ser Gly Leu Ala Leu Met Thr Thr Thr Ile Asn Ser Leu Val
        30                  35                  40

ATC GCT GCA ATT ATT GTG ACC CGG AAG CTG CAC CAT CCA GCC AAT TAT  795
Ile Ala Ala Ile Ile Val Thr Arg Lys Leu His His Pro Ala Asn Tyr
45                  50                  55                  60

TTA ATT TGT TCC CTT GCA GTC ACA GAT TTT CTT GTG GCT GTC CTG GTG  843
Leu Ile Cys Ser Leu Ala Val Thr Asp Phe Leu Val Ala Val Leu Val
                65                  70                  75

ATG CCC TTC AGC ATT GTG TAT ATT GTG AGA GAG AGC TGG ATT ATG GGG  891
Met Pro Phe Ser Ile Val Tyr Ile Val Arg Glu Ser Trp Ile Met Gly
                    80                  85                  90

CAA GTG GTC TGT GAC ATT TGG CTG AGT GTT GAC ATT ACC TGC TGC ACG  939
Gln Val Val Cys Asp Ile Trp Leu Ser Val Asp Ile Thr Cys Cys Thr
            95                  100                 105

TGC TCC ATC TTG CAT CTC TCA GCT ATA GCT TTG GAT CGG TAT CGA GCA  987
Cys Ser Ile Leu His Leu Ser Ala Ile Ala Leu Asp Arg Tyr Arg Ala
        110                 115                 120

ATC ACA GAT GCT GTT GAG TAT GCC AGG AAA AGG ACT CCA AAG CAT GCT  1035
Ile Thr Asp Ala Val Glu Tyr Ala Arg Lys Arg Thr Pro Lys His Ala
125                 130                 135                 140

GGC ATT ATG ATT ACA ATA GTT TGG ATT ATA TCT GTT TTT ATC TCT ATG  1083
Gly Ile Met Ile Thr Ile Val Trp Ile Ile Ser Val Phe Ile Ser Met
                145                 150                 155

CCT CCT CTA TTC TGG AGG CAC CAA GGA ACT AGC AGA GAT GAT GAA TGC  1131
Pro Pro Leu Phe Trp Arg His Gln Gly Thr Ser Arg Asp Asp Glu Cys
                160                 165                 170

ATC ATC AAG CAC GAC CAC ATT GTT TCC ACC ATT TAC TCA ACA TTT GGA  1179
Ile Ile Lys His Asp His Ile Val Ser Thr Ile Tyr Ser Thr Phe Gly
            175                 180                 185

GCT TTC TAC ATC CCA CTG GCA TTG ATT TTG ATC CTT TAC TAC AAA ATA  1227
Ala Phe Tyr Ile Pro Leu Ala Leu Ile Leu Ile Leu Tyr Tyr Lys Ile
        190                 195                 200

TAT AGA GCA GCA AAG ACA TTA TAC CAC AAG AGA CAA GCA AGT AGG ATT  1275
Tyr Arg Ala Ala Lys Thr Leu Tyr His Lys Arg Gln Ala Ser Arg Ile
205                 210                 215                 220

GCA AAG GAG GAG GTG AAT GGC CAA GTC CTT TTG GAG AGT GGT GAG AAA  1323
Ala Lys Glu Glu Val Asn Gly Gln Val Leu Leu Glu Ser Gly Glu Lys
                225                 230                 235

AGC ACT AAA TCA GTT TCC ACA TCC TAT GTA CTA GAA AAG TCT TTA TCT  1371
Ser Thr Lys Ser Val Ser Thr Ser Tyr Val Leu Glu Lys Ser Leu Ser
        240                 245                 250

| | | | | | | | | | | | | | | | | |
|---|---|---|---|---|---|---|---|---|---|---|---|---|---|---|---|---|
| GAC | CCA | TCA | ACA | GAC | TTT | GAT | AAA | ATT | CAT | AGC | ACA | GTG | AGA | AGT | CTC | 1419 |
| Asp | Pro | Ser | Thr | Asp | Phe | Asp | Lys | Ile | His | Ser | Thr | Val | Arg | Ser | Leu | |
| | | 255 | | | | 260 | | | | | 265 | | | | | |
| AGG | TCT | GAA | TTC | AAG | CAT | GAG | AAA | TCT | TGG | AGA | AGG | CAA | AAG | ATC | TCA | 1467 |
| Arg | Ser | Glu | Phe | Lys | His | Glu | Lys | Ser | Trp | Arg | Arg | Gln | Lys | Ile | Ser | |
| | 270 | | | | | 275 | | | | | 280 | | | | | |
| GGT | ACA | AGA | GAA | CGG | AAA | GCA | GCC | ACT | ACC | CTG | GGA | TTA | ATC | TTG | GGT | 1515 |
| Gly | Thr | Arg | Glu | Arg | Lys | Ala | Ala | Thr | Thr | Leu | Gly | Leu | Ile | Leu | Gly | |
| 285 | | | | | 290 | | | | | 295 | | | | | 300 | |
| GCA | TTT | GTA | ATA | TGT | TGG | CTT | CCT | TTT | TTT | GTA | AAA | GAA | TTA | GTT | GTT | 1563 |
| Ala | Phe | Val | Ile | Cys | Trp | Leu | Pro | Phe | Phe | Val | Lys | Glu | Leu | Val | Val | |
| | | | | 305 | | | | | 310 | | | | | 315 | | |
| AAT | GTC | TGT | GAC | AAA | TGT | AAA | ATT | TCT | GAA | GAA | ATG | TCC | AAT | TTT | TTG | 1611 |
| Asn | Val | Cys | Asp | Lys | Cys | Lys | Ile | Ser | Glu | Glu | Met | Ser | Asn | Phe | Leu | |
| | | | 320 | | | | | 325 | | | | | 330 | | | |
| GCA | TGG | CTT | GGG | TAT | CTC | AAT | TCC | CTT | ATA | AAT | CCA | CTG | ATT | TAC | ACA | 1659 |
| Ala | Trp | Leu | Gly | Tyr | Leu | Asn | Ser | Leu | Ile | Asn | Pro | Leu | Ile | Tyr | Thr | |
| | | 335 | | | | | 340 | | | | | 345 | | | | |
| ATC | TTT | AAT | GAA | GAC | TTC | AAG | AAA | GCA | TTC | CAA | AAG | CTT | GTG | CGA | TGT | 1707 |
| Ile | Phe | Asn | Glu | Asp | Phe | Lys | Lys | Ala | Phe | Gln | Lys | Leu | Val | Arg | Cys | |
| | 350 | | | | | 355 | | | | | 360 | | | | | |
| CGA | TGT | TAGTTTTAAA AATGTTT | | | | | | | | | | | | | | 1730 |
| Arg | Cys | | | | | | | | | | | | | | | |
| 365 | | | | | | | | | | | | | | | | |

( 2 ) INFORMATION FOR SEQ ID NO:2:

( i ) SEQUENCE CHARACTERISTICS:
        ( A ) LENGTH: 366 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Asp | Phe | Leu | Asn | Ser | Ser | Asp | Gln | Asn | Leu | Thr | Ser | Glu | Glu | Leu |
| 1 | | | | 5 | | | | | 10 | | | | | 15 | |
| Leu | Asn | Arg | Met | Pro | Ser | Lys | Ile | Leu | Val | Ser | Leu | Thr | Leu | Ser | Gly |
| | | | 20 | | | | | 25 | | | | | 30 | | |
| Leu | Ala | Leu | Met | Thr | Thr | Thr | Ile | Asn | Ser | Leu | Val | Ile | Ala | Ala | Ile |
| | | | 35 | | | | | 40 | | | | | 45 | | |
| Ile | Val | Thr | Arg | Lys | Leu | His | His | Pro | Ala | Asn | Tyr | Leu | Ile | Cys | Ser |
| | 50 | | | | | 55 | | | | | 60 | | | | |
| Leu | Ala | Val | Thr | Asp | Phe | Leu | Val | Ala | Val | Leu | Val | Met | Pro | Phe | Ser |
| 65 | | | | | 70 | | | | | 75 | | | | | 80 |
| Ile | Val | Tyr | Ile | Val | Arg | Glu | Ser | Trp | Ile | Met | Gly | Gln | Val | Val | Cys |
| | | | | 85 | | | | | 90 | | | | | 95 | |
| Asp | Ile | Trp | Leu | Ser | Val | Asp | Ile | Thr | Cys | Cys | Thr | Cys | Ser | Ile | Leu |
| | | | 100 | | | | | 105 | | | | | 110 | | |
| His | Leu | Ser | Ala | Ile | Ala | Leu | Asp | Arg | Tyr | Arg | Ala | Ile | Thr | Asp | Ala |
| | | 115 | | | | | 120 | | | | | 125 | | | |
| Val | Glu | Tyr | Ala | Arg | Lys | Arg | Thr | Pro | Lys | His | Ala | Gly | Ile | Met | Ile |
| | 130 | | | | | 135 | | | | | 140 | | | | |
| Thr | Ile | Val | Trp | Ile | Ile | Ser | Val | Phe | Ile | Ser | Met | Pro | Pro | Leu | Phe |
| 145 | | | | | 150 | | | | | 155 | | | | | 160 |
| Trp | Arg | His | Gln | Gly | Thr | Ser | Arg | Asp | Asp | Glu | Cys | Ile | Ile | Lys | His |
| | | | | 165 | | | | | 170 | | | | | 175 | |
| Asp | His | Ile | Val | Ser | Thr | Ile | Tyr | Ser | Thr | Phe | Gly | Ala | Phe | Tyr | Ile |
| | | | 180 | | | | | 185 | | | | | 190 | | |
| Pro | Leu | Ala | Leu | Ile | Leu | Ile | Leu | Tyr | Tyr | Lys | Ile | Tyr | Arg | Ala | Ala |

|     |     |     |     |     | 195 |     |     |     |     | 200 |     |     |     |     | 205 |     |     |
|-----|-----|-----|-----|-----|-----|-----|-----|-----|-----|-----|-----|-----|-----|-----|-----|-----|-----|

Lys Thr Leu Tyr His Lys Arg Gln Ala Ser Arg Ile Ala Lys Glu Glu
210                     215                 220

Val Asn Gly Gln Val Leu Leu Glu Ser Gly Glu Lys Ser Thr Lys Ser
225                 230                 235                 240

Val Ser Thr Ser Tyr Val Leu Glu Lys Ser Leu Ser Asp Pro Ser Thr
                245                 250                 255

Asp Phe Asp Lys Ile His Ser Thr Val Arg Ser Leu Arg Ser Glu Phe
            260                 265                 270

Lys His Glu Lys Ser Trp Arg Arg Gln Lys Ile Ser Gly Thr Arg Glu
        275                 280                 285

Arg Lys Ala Ala Thr Thr Leu Gly Leu Ile Leu Gly Ala Phe Val Ile
    290                 295                 300

Cys Trp Leu Pro Phe Phe Val Lys Glu Leu Val Val Asn Val Cys Asp
305                 310                 315                 320

Lys Cys Lys Ile Ser Glu Glu Met Ser Asn Phe Leu Ala Trp Leu Gly
                325                 330                 335

Tyr Leu Asn Ser Leu Ile Asn Pro Leu Ile Tyr Thr Ile Phe Asn Glu
            340                 345                 350

Asp Phe Lys Lys Ala Phe Gln Lys Leu Val Arg Cys Arg Cys
        355                 360                 365

(2) INFORMATION FOR SEQ ID NO:3:

(i) SEQUENCE CHARACTERISTICS:
        (A) LENGTH: 422 amino acids
        (B) TYPE: amino acid
        (C) STRANDEDNESS: unknown
        (D) TOPOLOGY: linear (ii) MOLECULE TYPE: protein (iii) HYPOTHETICAL: NO (iv) ANTI-SENSE: NO (v) FRAGMENT TYPE: N-terminal (vii) IMMEDIATE SOURCE:
        (B) CLONE: 5-HT1A (xi) SEQUENCE DESCRIPTION: SEQ ID NO:3:

Met Asp Val Leu Ser Pro Gly Gln Gly Asn Asn Thr Thr Ser Pro Pro
1               5                   10                  15

Ala Pro Phe Glu Thr Gly Gly Asn Thr Thr Gly Ile Ser Asp Val Thr
            20                  25                  30

Val Ser Tyr Gln Val Ile Thr Ser Leu Leu Leu Gly Thr Leu Ile Phe
        35                  40                  45

Cys Ala Val Leu Gly Asn Ala Cys Val Val Ala Ala Ile Ala Leu Glu
    50                  55                  60

Arg Ser Leu Gln Asn Val Ala Asn Tyr Leu Ile Gly Ser Leu Ala Val
65                  70                  75                  80

Thr Asp Leu Met Val Ser Val Leu Val Leu Pro Met Ala Ala Leu Tyr
                85                  90                  95

Gln Val Leu Asn Lys Trp Thr Leu Gly Gln Val Thr Cys Asp Leu Phe
            100                 105                 110

Ile Ala Leu Asp Val Leu Cys Cys Thr Ser Ser Ile Leu His Leu Cys
        115                 120                 125

Ala Ile Ala Leu Asp Arg Tyr Trp Ala Ile Thr Asp Pro Ile Asp Tyr
    130                 135                 140

Val Asn Lys Arg Thr Pro Arg Arg Ala Ala Ala Leu Ile Ser Leu Thr

|     |     |     |     |     |     |     |     |     |     |     |     |     |     |     |     |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |
| Trp | Leu | Ile | Gly | Phe | Leu | Ile | Ser | Ile | Pro | Pro | Met | Leu | Gly | Trp | Arg |
|     |     |     |     | 165 |     |     |     |     | 170 |     |     |     |     | 175 |     |
| Thr | Pro | Glu | Asp | Arg | Ser | Asp | Pro | Asp | Ala | Cys | Thr | Ile | Ser | Lys | Asp |
|     |     |     | 180 |     |     |     |     | 185 |     |     |     |     | 190 |     |     |
| His | Gly | Tyr | Thr | Ile | Tyr | Ser | Thr | Phe | Gly | Ala | Phe | Tyr | Ile | Pro | Leu |
|     |     | 195 |     |     |     |     | 200 |     |     |     |     | 205 |     |     |     |
| Leu | Leu | Met | Leu | Val | Leu | Tyr | Gly | Arg | Ile | Phe | Arg | Ala | Ala | Arg | Phe |
|     | 210 |     |     |     |     | 215 |     |     |     |     | 220 |     |     |     |     |
| Arg | Ile | Arg | Lys | Thr | Val | Lys | Lys | Val | Glu | Lys | Thr | Gly | Ala | Asp | Thr |
| 225 |     |     |     |     | 230 |     |     |     |     | 235 |     |     |     |     | 240 |
| Arg | His | Gly | Ala | Ser | Pro | Ala | Pro | Gln | Pro | Lys | Lys | Ser | Val | Asn | Gly |
|     |     |     |     | 245 |     |     |     |     | 250 |     |     |     |     | 255 |     |
| Glu | Ser | Gly | Ser | Arg | Asn | Trp | Arg | Leu | Gly | Val | Glu | Ser | Lys | Ala | Gly |
|     |     |     | 260 |     |     |     |     | 265 |     |     |     |     | 270 |     |     |
| Gly | Ala | Leu | Cys | Ala | Asn | Gly | Ala | Val | Arg | Gln | Gly | Asp | Asp | Gly | Ala |
|     |     |     |     | 275 |     |     |     |     | 280 |     |     |     |     | 285 |     |
| Ala | Leu | Glu | Val | Ile | Glu | Val | His | Arg | Val | Gly | Asn | Ser | Lys | Glu | His |
|     | 290 |     |     |     |     | 295 |     |     |     |     | 300 |     |     |     |     |
| Leu | Pro | Leu | Pro | Ser | Glu | Ala | Gly | Pro | Thr | Pro | Cys | Ala | Pro | Ala | Ser |
| 305 |     |     |     |     | 310 |     |     |     |     | 315 |     |     |     |     | 320 |
| Phe | Glu | Arg | Lys | Asn | Glu | Arg | Asn | Ala | Glu | Ala | Lys | Arg | Lys | Met | Ala |
|     |     |     |     | 325 |     |     |     |     | 330 |     |     |     |     | 335 |     |
| Leu | Ala | Arg | Glu | Arg | Lys | Thr | Val | Lys | Thr | Leu | Gly | Ile | Ile | Met | Gly |
|     |     |     | 340 |     |     |     |     | 345 |     |     |     |     | 350 |     |     |
| Thr | Phe | Ile | Leu | Cys | Trp | Leu | Pro | Phe | Phe | Ile | Val | Ala | Leu | Val | Leu |
|     |     | 355 |     |     |     |     | 360 |     |     |     |     | 365 |     |     |     |
| Pro | Phe | Cys | Glu | Ser | Ser | Cys | His | Met | Pro | Thr | Leu | Leu | Gly | Ala | Ile |
|     | 370 |     |     |     |     | 375 |     |     |     |     | 380 |     |     |     |     |
| Ile | Asn | Trp | Leu | Gly | Tyr | Ser | Asn | Ser | Leu | Leu | Asn | Pro | Val | Ile | Tyr |
| 385 |     |     |     |     | 390 |     |     |     |     | 395 |     |     |     |     | 400 |
| Ala | Tyr | Phe | Asn | Lys | Asp | Phe | Gln | Asn | Ala | Phe | Lys | Lys | Ile | Ile | Lys |
|     |     |     |     | 405 |     |     |     |     | 410 |     |     |     |     | 415 |     |
| Cys | Leu | Phe | Cys | Arg | Gln |     |     |     |     |     |     |     |     |     |     |
|     |     |     | 420 |     |     |     |     |     |     |     |     |     |     |     |     |

( 2 ) INFORMATION FOR SEQ ID NO:4:

( i ) SEQUENCE CHARACTERISTICS:
        ( A ) LENGTH: 460 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i i ) IMMEDIATE SOURCE:
        ( B ) CLONE: 5-HT1C ( x i ) SEQUENCE DESCRIPTION: SEQ ID NO:4:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Val | Asn | Leu | Gly | Asn | Ala | Val | Arg | Ser | Leu | Leu | Met | His | Leu | Ile |
| 1   |     |     |     | 5   |     |     |     |     | 10  |     |     |     |     | 15  |     |
| Gly | Leu | Leu | Val | Trp | Gln | Phe | Asp | Ile | Ser | Ile | Ser | Pro | Val | Ala | Ala |
|     |     |     | 20  |     |     |     |     | 25  |     |     |     |     | 30  |     |     |
| Ile | Val | Thr | Asp | Thr | Phe | Asn | Ser | Ser | Asp | Gly | Gly | Arg | Leu | Phe | Gln |

-continued

```
            35                          40                            45
Phe   Pro   Asp   Gly   Val   Gln   Asn   Trp   Pro   Ala   Leu   Ser   Ile   Val   Val   Ile
      50                      55                      60
Ile   Ile   Met   Thr   Ile   Gly   Gly   Asn   Ile   Leu   Val   Ile   Met   Ala   Val   Ser
65                            70                      75                                  80
Met   Glu   Lys   Lys   Leu   His   Asn   Ala   Thr   Asn   Tyr   Phe   Leu   Met   Ser   Leu
                        85                            90                            95
Ala   Ile   Ala   Asp   Met   Leu   Val   Gly   Leu   Leu   Val   Met   Pro   Leu   Ser   Leu
                  100                         105                       110
Leu   Ala   Ile   Leu   Tyr   Asp   Tyr   Val   Trp   Pro   Leu   Pro   Arg   Tyr   Leu   Cys
            115                         120                       125
Pro   Val   Trp   Ile   Ser   Leu   Asp   Val   Leu   Phe   Ser   Thr   Ala   Ser   Ile   Met
      130                         135                       140
His   Leu   Cys   Ala   Ile   Ser   Leu   Asp   Arg   Tyr   Val   Ala   Ile   Arg   Asn   Pro
145                           150                         155                             160
Ile   Glu   His   Ser   Arg   Phe   Asn   Ser   Arg   Thr   Lys   Ala   Ile   Met   Lys   Ile
                        165                             170                       175
Ala   Ile   Val   Trp   Ala   Ile   Ser   Ile   Gly   Val   Ser   Val   Pro   Ile   Pro   Val
                  180                         185                       190
Ile   Gly   Leu   Arg   Asp   Glu   Ser   Lys   Val   Phe   Val   Asn   Asn   Thr   Thr   Cys
            195                         200                       205
Val   Leu   Asn   Asp   Pro   Asn   Phe   Val   Leu   Ile   Gly   Ser   Phe   Val   Ala   Phe
      210                         215                       220
Phe   Ile   Pro   Leu   Thr   Ile   Met   Val   Ile   Thr   Tyr   Phe   Leu   Thr   Ile   Tyr
225                           230                         235                             240
Val   Leu   Arg   Arg   Gln   Thr   Leu   Met   Leu   Leu   Arg   Gly   His   Thr   Glu   Glu
                        245                             250                       255
Glu   Leu   Ala   Asn   Met   Ser   Leu   Asn   Phe   Leu   Asn   Cys   Cys   Cys   Lys   Lys
                  260                         265                       270
Asn   Gly   Gly   Glu   Glu   Glu   Asn   Ala   Pro   Asn   Pro   Asn   Pro   Asp   Gln   Lys
            275                         280                       285
Pro   Arg   Arg   Lys   Lys   Lys   Glu   Lys   Arg   Pro   Arg   Gly   Thr   Met   Gln   Ala
      290                         295                       300
Ile   Asn   Asn   Glu   Lys   Lys   Ala   Ser   Lys   Val   Leu   Gly   Ile   Val   Phe   Phe
305                           310                         315                             320
Val   Phe   Leu   Ile   Met   Trp   Cys   Pro   Phe   Phe   Ile   Thr   Asn   Ile   Leu   Ser
                        325                             330                       335
Val   Leu   Cys   Gly   Lys   Ala   Cys   Asn   Gln   Lys   Leu   Met   Glu   Lys   Leu   Leu
                  340                         345                       350
Asn   Val   Phe   Val   Trp   Ile   Gly   Tyr   Val   Cys   Ser   Gly   Ile   Asn   Pro   Leu
            355                         360                       365
Val   Tyr   Thr   Leu   Phe   Asn   Lys   Ile   Tyr   Arg   Arg   Ala   Phe   Ser   Lys   Tyr
      370                         375                       380
Leu   Arg   Cys   Asp   Tyr   Lys   Pro   Asp   Lys   Lys   Pro   Pro   Val   Arg   Gln   Ile
385                           390                         395                             400
Pro   Arg   Val   Ala   Ala   Thr   Ala   Leu   Ser   Gly   Arg   Glu   Leu   Asn   Val   Asn
                        405                             410                       415
Ile   Tyr   Arg   His   Thr   Asn   Glu   Arg   Val   Ala   Arg   Lys   Ala   Asn   Asp   Pro
                  420                         425                       430
Glu   Pro   Gly   Ile   Glu   Met   Gln   Val   Glu   Asn   Leu   Glu   Leu   Pro   Val   Asn
            435                         440                       445
Pro   Ser   Asn   Val   Val   Ser   Glu   Arg   Ile   Ser   Ser   Val
      450                         455                       460
```

( 2 ) INFORMATION FOR SEQ ID NO:5:

( i ) SEQUENCE CHARACTERISTICS:
    ( A ) LENGTH: 376 amino acids
    ( B ) TYPE: amino acid
    ( C ) STRANDEDNESS: unknown
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i i ) IMMEDIATE SOURCE:
    ( B ) CLONE: 5-HT1DA ( x i ) SEQUENCE DESCRIPTION: SEQ ID NO:5:

```
Met Ser Pro Leu Asn Gln Ser Ala Glu Gly Leu Pro Gln Glu Ala Ser
 1               5                  10                  15

Asn Arg Ser Leu Asn Ala Thr Glu Thr Ser Glu Ala Trp Asp Pro Arg
                20                  25                  30

Thr Leu Gln Ala Leu Lys Ile Ser Leu Pro Val Leu Leu Ser Val Ile
            35                  40                  45

Thr Leu Ala Thr Val Leu Ser Asn Ala Phe Val Leu Thr Thr Ile Leu
        50                  55                  60

Leu Thr Arg Lys Leu His Thr Pro Ala Asn Tyr Leu Ile Gly Ser Leu
65                  70                  75                  80

Ala Thr Thr Asp Leu Leu Val Ser Ile Leu Val Met Pro Ile Ser Met
                85                  90                  95

Ala Tyr Thr Ile Thr His Thr Trp Asn Phe Gly Gln Ile Leu Cys Asp
               100                 105                 110

Ile Trp Leu Ser Ser Asp Ile Thr Cys Cys Thr Ala Ser Ile Leu His
            115                 120                 125

Leu Cys Val Ile Ala Leu Asp Arg Tyr Trp Ala Ile Thr Asp Ala Leu
        130                 135                 140

Glu Tyr Ser Lys Arg Arg Thr Ala Gly His Ala Ala Thr Met Ile Ala
145                 150                 155                 160

Ile Val Trp Ala Ile Ser Ile Cys Ile Ser Ile Pro Pro Leu Phe Trp
                165                 170                 175

Arg Gln Glu Lys Ala Gln Glu Glu Met Ser Asp Cys Leu Val Asn Thr
               180                 185                 190

Ser Gln Ile Ser Tyr Thr Ile Tyr Ser Thr Cys Gly Ala Phe Tyr Ile
            195                 200                 205

Pro Ser Val Leu Leu Ile Ile Leu Tyr Gly Arg Ile Tyr Arg Ala Ala
        210                 215                 220

Arg Asn Arg Ile Leu Asn Pro Pro Ser Leu Ser Gly Lys Arg Phe Thr
225                 230                 235                 240

Thr Ala His Leu Ile Thr Gly Ser Ala Gly Ser Val Cys Ser Leu Asn
                245                 250                 255

Ser Ser Leu His Glu Gly His Ser His Ser Ala Gly Ser Pro Leu Phe
               260                 265                 270

Phe Asn His Val Lys Ile Lys Leu Ala Asp Ser Ala Leu Glu Arg Lys
            275                 280                 285

Arg Ile Ser Ala Ala Arg Glu Arg Lys Ala Thr Lys Ile Leu Gly Ile
        290                 295                 300

Ile Leu Gly Ala Phe Ile Ile Cys Trp Leu Pro Phe Phe Val Val Ser
305                 310                 315                 320

Leu Val Leu Pro Ile Cys Arg Asp Ser Cys Trp Ile His Pro Gly Leu
                325                 330                 335
```

```
      Phe  Asp  Phe  Phe  Thr  Trp  Leu  Gly  Tyr  Leu  Asn  Ser  Leu  Ile  Asn  Pro
                      340                     345                     350

Ile  Ile  Tyr  Thr  Val  Phe  Asn  Glu  Glu  Phe  Arg  Gln  Ala  Phe  Gln  Lys
                      355                     360                     365

Ile  Val  Pro  Phe  Arg  Lys  Ala  Ser
                      370                 375
```

( 2 ) INFORMATION FOR SEQ ID NO:6:

( i ) SEQUENCE CHARACTERISTICS:
        ( A ) LENGTH: 390 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i i ) IMMEDIATE SOURCE:
        ( B ) CLONE: 5-HT1DB ( x i ) SEQUENCE DESCRIPTION: SEQ ID NO:6:

```
      Met  Glu  Glu  Pro  Gly  Ala  Gln  Cys  Ala  Pro  Pro  Ala  Pro  Ala  Gly  Ser
      1                   5                        10                      15

Glu  Thr  Trp  Val  Pro  Gln  Ala  Asn  Leu  Ser  Ser  Ala  Pro  Ser  Gln  Asn
                      20                      25                      30

Cys  Ser  Ala  Lys  Asp  Tyr  Ile  Tyr  Gln  Asp  Ser  Ile  Ser  Leu  Pro  Trp
                35                      40                      45

Lys  Val  Leu  Leu  Val  Met  Leu  Leu  Ala  Leu  Ile  Thr  Leu  Ala  Thr  Thr
                50                      55                      60

Leu  Ser  Asn  Ala  Phe  Val  Ile  Ala  Thr  Val  Tyr  Arg  Thr  Arg  Lys  Leu
      65                       70                      75                       80

His  Thr  Pro  Ala  Asn  Tyr  Leu  Ile  Ala  Ser  Leu  Asp  Val  Thr  Asp  Leu
                          85                      90                      95

Leu  Val  Ser  Ile  Leu  Val  Ile  Pro  Ile  Ser  Thr  Met  Tyr  Thr  Val  Thr
                      100                     105                     110

Asp  Arg  Trp  Thr  Leu  Ser  Gln  Val  Val  Cys  Asp  Phe  Trp  Leu  Ser  Ser
                      115                     120                     125

Asp  Ile  Thr  Cys  Cys  Thr  Ala  Ser  Ile  Leu  His  Leu  Cys  Val  Ile  Ala
                130                     135                     140

Leu  Asp  Arg  Tyr  Trp  Ala  Ile  Thr  Asp  Ala  Val  Glu  Tyr  Ser  Ala  Lys
      145                      150                     155                      160

Arg  Thr  Pro  Lys  Arg  Ala  Ala  Val  Met  Ile  Ala  Leu  Val  Trp  Val  Phe
                      165                     170                     175

Ser  Ile  Ser  Ile  Ser  Leu  Pro  Pro  Phe  Phe  Trp  Arg  Gln  Ala  Lys  Ala
                      180                     185                     190

Glu  Glu  Glu  Val  Ser  Glu  Cys  Val  Val  Asn  Thr  Asp  His  Ile  Leu  Tyr
                      195                     200                     205

Thr  Val  Tyr  Ser  Thr  Val  Gly  Ala  Phe  Tyr  Phe  Pro  Thr  Leu  Leu  Leu
                210                     215                     220

Ile  Ala  Leu  Tyr  Gly  Arg  Ile  Tyr  Val  Glu  Ala  Arg  Ser  Arg  Ile  Leu
      225                      230                     235                      240

Lys  Gln  Thr  Pro  Asn  Arg  Thr  Gly  Lys  Arg  Leu  Thr  Arg  Ala  Gln  Leu
                      245                     250                     255

Ile  Thr  Asp  Ser  Pro  Gly  Ser  Thr  Ser  Ser  Val  Thr  Ser  Ile  Asn  Ser
                      260                     265                     270
```

```
Arg  Val  Pro  Asp  Val  Pro  Ser  Glu  Ser  Gly  Ser  Pro  Val  Tyr  Val  Asn
          275                 280                      285

Gln  Val  Lys  Val  Arg  Val  Ser  Asp  Ala  Leu  Leu  Glu  Lys  Lys  Lys  Leu
     290                      295                      300

Met  Ala  Ala  Arg  Glu  Arg  Lys  Ala  Thr  Lys  Thr  Leu  Gly  Ile  Ile  Leu
305                      310                 315                           320

Gly  Ala  Phe  Ile  Val  Cys  Trp  Leu  Pro  Phe  Phe  Ile  Ile  Ser  Leu  Val
                    325                 330                      335

Met  Pro  Ile  Cys  Lys  Asp  Ala  Cys  Trp  Phe  His  Leu  Ala  Ile  Phe  Asp
               340                 345                      350

Phe  Phe  Thr  Trp  Leu  Gly  Tyr  Leu  Asn  Ser  Leu  Ile  Asn  Pro  Ile  Ile
          355                 360                      365

Tyr  Thr  Met  Ser  Asn  Glu  Asp  Phe  Lys  Gln  Ala  Phe  His  Lys  Leu  Ile
          370                 375                      380

Arg  Phe  Lys  Cys  Thr  Ser
385                 390
```

( 2 ) INFORMATION FOR SEQ ID NO:7:

( i ) SEQUENCE CHARACTERISTICS:
        ( A ) LENGTH: 366 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i i ) IMMEDIATE SOURCE:
        ( B ) CLONE: 5-HT1F ( x i ) SEQUENCE DESCRIPTION: SEQ ID NO:7:

```
Met  Asp  Phe  Leu  Asn  Ser  Ser  Asp  Gln  Asn  Leu  Thr  Ser  Glu  Glu  Leu
1                   5                      10                      15

Leu  Asn  Arg  Met  Pro  Ser  Lys  Ile  Leu  Val  Ser  Leu  Thr  Leu  Ser  Gly
               20                      25                      30

Leu  Ala  Leu  Met  Thr  Thr  Thr  Ile  Asn  Ser  Leu  Val  Ile  Ala  Ala  Ile
          35                      40                      45

Ile  Val  Thr  Arg  Lys  Leu  His  His  Pro  Ala  Asn  Tyr  Leu  Ile  Cys  Ser
     50                      55                      60

Leu  Ala  Val  Thr  Asp  Phe  Leu  Val  Ala  Val  Leu  Val  Met  Pro  Phe  Ser
65                       70                      75                       80

Ile  Val  Tyr  Ile  Val  Arg  Glu  Ser  Trp  Ile  Met  Gly  Gln  Val  Val  Cys
               85                      90                      95

Asp  Ile  Trp  Leu  Ser  Val  Asp  Ile  Thr  Cys  Cys  Thr  Cys  Ser  Ile  Leu
          100                     105                     110

His  Leu  Ser  Ala  Ile  Ala  Leu  Asp  Arg  Tyr  Arg  Ala  Ile  Thr  Asp  Ala
          115                     120                     125

Val  Glu  Tyr  Ala  Arg  Lys  Arg  Thr  Pro  Lys  His  Ala  Gly  Ile  Met  Ile
     130                     135                     140

Thr  Ile  Val  Trp  Ile  Ile  Ser  Val  Phe  Ile  Ser  Met  Pro  Pro  Leu  Phe
145                     150                     155                     160

Trp  Arg  His  Gln  Gly  Thr  Ser  Arg  Asp  Asp  Glu  Cys  Ile  Ile  Lys  His
               165                     170                     175

Asp  His  Ile  Val  Ser  Thr  Ile  Tyr  Ser  Thr  Phe  Gly  Ala  Phe  Tyr  Ile
          180                     185                     190
```

| Pro | Leu | Ala | Leu | Ile | Leu | Ile | Leu | Tyr | Tyr | Lys | Ile | Tyr | Arg | Ala | Ala |
|---|---|---|---|---|---|---|---|---|---|---|---|---|---|---|---|
| | | 195 | | | | 200 | | | | 205 | | | | | |
| Lys | Thr | Leu | Tyr | His | Lys | Arg | Gln | Ala | Ser | Arg | Ile | Ala | Lys | Glu | Glu |
| | 210 | | | | | 215 | | | | | 220 | | | | |
| Val | Asn | Gly | Gln | Val | Leu | Leu | Glu | Ser | Gly | Glu | Lys | Ser | Thr | Lys | Ser |
| 225 | | | | | 230 | | | | | 235 | | | | | 240 |
| Val | Ser | Thr | Ser | Tyr | Val | Leu | Glu | Lys | Ser | Leu | Ser | Asp | Pro | Ser | Thr |
| | | | | 245 | | | | | 250 | | | | | 255 | |
| Asp | Phe | Asp | Lys | Ile | His | Ser | Thr | Val | Arg | Ser | Leu | Arg | Ser | Glu | Phe |
| | | | 260 | | | | | 265 | | | | | 270 | | |
| Lys | His | Glu | Lys | Ser | Trp | Arg | Arg | Gln | Lys | Ile | Ser | Gly | Thr | Arg | Glu |
| | | 275 | | | | | 280 | | | | | 285 | | | |
| Arg | Lys | Ala | Ala | Thr | Thr | Leu | Gly | Leu | Ile | Leu | Gly | Ala | Phe | Val | Ile |
| | 290 | | | | | 295 | | | | | 300 | | | | |
| Cys | Trp | Leu | Pro | Phe | Phe | Val | Lys | Glu | Leu | Val | Val | Asn | Val | Cys | Asp |
| 305 | | | | | 310 | | | | | 315 | | | | | 320 |
| Lys | Cys | Lys | Ile | Ser | Glu | Glu | Met | Ser | Asn | Phe | Leu | Ala | Trp | Leu | Gly |
| | | | | 325 | | | | | 330 | | | | | 335 | |
| Tyr | Leu | Asn | Ser | Leu | Ile | Asn | Pro | Leu | Ile | Tyr | Thr | Ile | Phe | Asn | Glu |
| | | | 340 | | | | | 345 | | | | | 350 | | |
| Asp | Phe | Lys | Lys | Ala | Phe | Gln | Lys | Leu | Val | Arg | Cys | Arg | Cys | | |
| | | 355 | | | | | 360 | | | | | 365 | | | |

( 2 ) INFORMATION FOR SEQ ID NO:8:

( i ) SEQUENCE CHARACTERISTICS:
        ( A ) LENGTH: 471 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i i ) IMMEDIATE SOURCE:
        ( B ) CLONE: 5-HT2

( x i ) SEQUENCE DESCRIPTION: SEQ ID NO:8:

| Met | Asp | Ile | Leu | Cys | Glu | Glu | Asn | Thr | Ser | Leu | Ser | Ser | Thr | Thr | Asn |
|---|---|---|---|---|---|---|---|---|---|---|---|---|---|---|---|
| 1 | | | | 5 | | | | | 10 | | | | | 15 | |
| Ser | Leu | Met | Gln | Leu | Asn | Asp | Asp | Thr | Arg | Leu | Tyr | Ser | Asn | Asp | Phe |
| | | | 20 | | | | | 25 | | | | | 30 | | |
| Asn | Ser | Gly | Glu | Ala | Asn | Thr | Ser | Asp | Ala | Phe | Asn | Trp | Thr | Val | Asp |
| | | 35 | | | | | 40 | | | | | 45 | | | |
| Ser | Glu | Asn | Arg | Thr | Asn | Leu | Ser | Cys | Glu | Gly | Cys | Leu | Ser | Pro | Ser |
| | 50 | | | | | 55 | | | | | 60 | | | | |
| Cys | Leu | Ser | Leu | Leu | His | Leu | Gln | Glu | Lys | Asn | Trp | Ser | Ala | Leu | Leu |
| 65 | | | | | 70 | | | | | 75 | | | | | 80 |
| Thr | Ala | Val | Val | Ile | Ile | Leu | Thr | Ile | Ala | Gly | Asn | Ile | Leu | Val | Ile |
| | | | | 85 | | | | | 90 | | | | | 95 | |
| Met | Ala | Val | Ser | Leu | Glu | Lys | Lys | Leu | Gln | Asn | Ala | Thr | Asn | Tyr | Phe |
| | | | 100 | | | | | 105 | | | | | 110 | | |
| Leu | Met | Ser | Leu | Ala | Ile | Ala | Asp | Met | Leu | Leu | Gly | Phe | Leu | Val | Met |
| | | 115 | | | | | 120 | | | | | 125 | | | |
| Pro | Val | Ser | Met | Leu | Thr | Ile | Leu | Tyr | Gly | Tyr | Arg | Trp | Pro | Leu | Pro |
| | 130 | | | | | 135 | | | | | 140 | | | | |

| | | | | | | | | | | | | | | |
|---|---|---|---|---|---|---|---|---|---|---|---|---|---|---|
| Ser 145 | Lys | Leu | Cys | Ala | Val 150 | Trp | Ile | Tyr | Leu | Asp 155 | Val | Leu | Phe | Ser Thr 160 |
| Ala | Ser | Ile | Met | His 165 | Leu | Cys | Ala | Ile | Ser 170 | Leu | Asp | Arg | Tyr | Val Ala 175 |
| Ile | Gln | Asn | Pro 180 | Ile | His | His | Ser | Arg 185 | Phe | Asn | Ser | Arg | Thr 190 | Lys Ala |
| Phe | Leu | Lys 195 | Ile | Ile | Ala | Val | Thr 200 | Ile | Ser | Val | Gly 205 | Ile | Ser Met |
| Pro | Ile 210 | Pro | Val | Phe | Gly | Leu 215 | Gln | Asp | Asp | Ser | Lys 220 | Val | Phe | Lys Glu |
| Gly 225 | Ser | Cys | Leu | Leu | Ala 230 | Asp | Asp | Asn | Phe | Val 235 | Leu | Ile | Gly | Ser Phe 240 |
| Val | Ser | Phe | Phe | Ile 245 | Pro | Leu | Thr | Ile | Met 250 | Val | Ile | Thr | Tyr | Phe Leu 255 |
| Thr | Ile | Lys | Ser 260 | Leu | Gln | Lys | Glu | Ala 265 | Thr | Leu | Cys | Val | Ser 270 | Asp Leu |
| Gly | Thr | Arg 275 | Ala | Lys | Leu | Ala | Ser 280 | Phe | Ser | Phe | Leu | Pro 285 | Gln | Ser Ser |
| Leu | Ser 290 | Ser | Glu | Lys | Leu | Phe 295 | Gln | Arg | Ser | Ile | His 300 | Arg | Glu | Pro Gly |
| Ser 305 | Tyr | Thr | Gly | Arg | Arg 310 | Thr | Met | Gln | Ser | Ile 315 | Ser | Asn | Glu | Gln Lys 320 |
| Ala | Cys | Lys | Val | Leu 325 | Gly | Ile | Val | Phe | Phe 330 | Leu | Phe | Val | Val | Met Trp 335 |
| Cys | Pro | Phe | Phe 340 | Ile | Thr | Asn | Ile | Met 345 | Ala | Val | Ile | Cys | Lys 350 | Glu Ser |
| Cys | Asn | Glu 355 | Asp | Val | Ile | Gly | Ala 360 | Leu | Leu | Asn | Val | Phe 365 | Val | Trp Ile |
| Gly | Tyr 370 | Leu | Ser | Ser | Ala | Val 375 | Asn | Pro | Leu | Val | Tyr 380 | Thr | Leu | Phe Asn |
| Lys 385 | Thr | Tyr | Arg | Ser | Ala 390 | Phe | Ser | Arg | Tyr | Ile 395 | Gln | Cys | Gln | Tyr Lys 400 |
| Glu | Asn | Lys | Lys | Pro 405 | Leu | Gln | Leu | Ile | Leu 410 | Val | Asn | Thr | Ile | Pro Ala 415 |
| Leu | Ala | Tyr | Lys 420 | Ser | Ser | Gln | Leu | Gln 425 | Met | Gly | Gln | Lys | Lys 430 | Asn Ser |
| Lys | Gln | Asp 435 | Ala | Lys | Thr | Thr | Asp 440 | Asn | Asp | Cys | Ser | Met 445 | Val | Ala Leu |
| Gly | Lys 450 | Gln | His | Ser | Glu | Glu 455 | Ala | Ser | Lys | Asp | Asn 460 | Ser | Asp | Gly Val |
| Asn 465 | Glu | Lys | Val | Ser | Cys 470 | Val | | | | | | | | |

( 2 ) INFORMATION FOR SEQ ID NO:9:

( i ) SEQUENCE CHARACTERISTICS:
        ( A ) LENGTH: 45 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: YES ( v i ) ORIGINAL SOURCE:
        ( A ) ORGANISM: ANTISENSE OLIGO -continued (xi) SEQUENCE DESCRIPTION: SEQ ID NO:9:

TCTCACCACT CTCCAAAAGG ACTTGGCCAT TCACCTCCTC CTTTG   45